(12) United States Patent
Crouzet et al.

(10) Patent No.: US 6,207,150 B1
(45) Date of Patent: Mar. 27, 2001

(54) VARIANTS OF THYMIDINE KINASE, NUCLEIC ACIDS ENCODING THEM, AND METHODS OF USING THEM

(75) Inventors: Joël Crouzet, Sceaux; Francis Blanche, Paris; Michel Couder, Sucy en Brie; Béatrice Cameron, Paris, all of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/125,099
(22) PCT Filed: Jan. 31, 1997
(86) PCT No.: PCT/ER97/00193
§ 371 Date: Aug. 6, 1998
§ 102(e) Date: Aug. 6, 1998
(87) PCT Pub. No.: WO97/29196
PCT Pub. Date: Aug. 14, 1997

(30) Foreign Application Priority Data

Feb. 9, 1996 (FR) .................................................. 96 01603
Aug. 1, 1996 (FR) .................................................. 96 09709

(51) Int. Cl.[7] .............................. A61K 38/51; C12N 9/12; C12N 15/00; C07H 21/04; C12Q 1/68
(52) U.S. Cl. ......................... 424/94.5; 435/194; 435/325; 435/252.3; 435/320.1; 435/6; 536/23.2
(58) Field of Search ................................ 514/44; 435/194, 435/320.1, 6, 252.3, 325; 536/23.2; 424/94.5

(56) References Cited

U.S. PATENT DOCUMENTS 5,877,010 * 3/1999 Leob et al. .................... 435/320.1

FOREIGN PATENT DOCUMENTS

WO 95/30007   11/1995 (WO) .

OTHER PUBLICATIONS

Salomon et al., A Truncated Herpes simplex Virus Thymidine Kinase Phosphorylates Thymidine and Nucleoside Analogs and Does Not Cause Sterility in Transgenic Mice, Molecular and Cellular Biology (15) 10: 5322–5328 (1995).
Michael et al., Site–directed mutagenesis of Herpes Simplex VLirus type 1 thymidine kinase opposes the importance of amino acid positions 251,321 and 348 for selective recognition of substrate analogs, Biochem.Biophys. Res. Comm. 209(3) 966–973 (1995).

* cited by examiner

*Primary Examiner*—Rebecca E. Prouty
*Assistant Examiner*—M S Monshipouri
(74) *Attorney, Agent, or Firm*—Brobeck, Phleger & Harrison, LLP

(57) ABSTRACT

The present invention relates to a nucleic acid sequence characterized in that it is derived from the wild nucleic acid sequence coding for a thymidine kinase, said nucleic acid sequence having at least one mutation in the region corresponding to the ATP binding site and conveniently a second mutation in the N-terminal region and/or C-terminal region. It also relates to variants of the wild thymidine kinase and their use in genic therapy.

37 Claims, 4 Drawing Sheets

Figure 1:
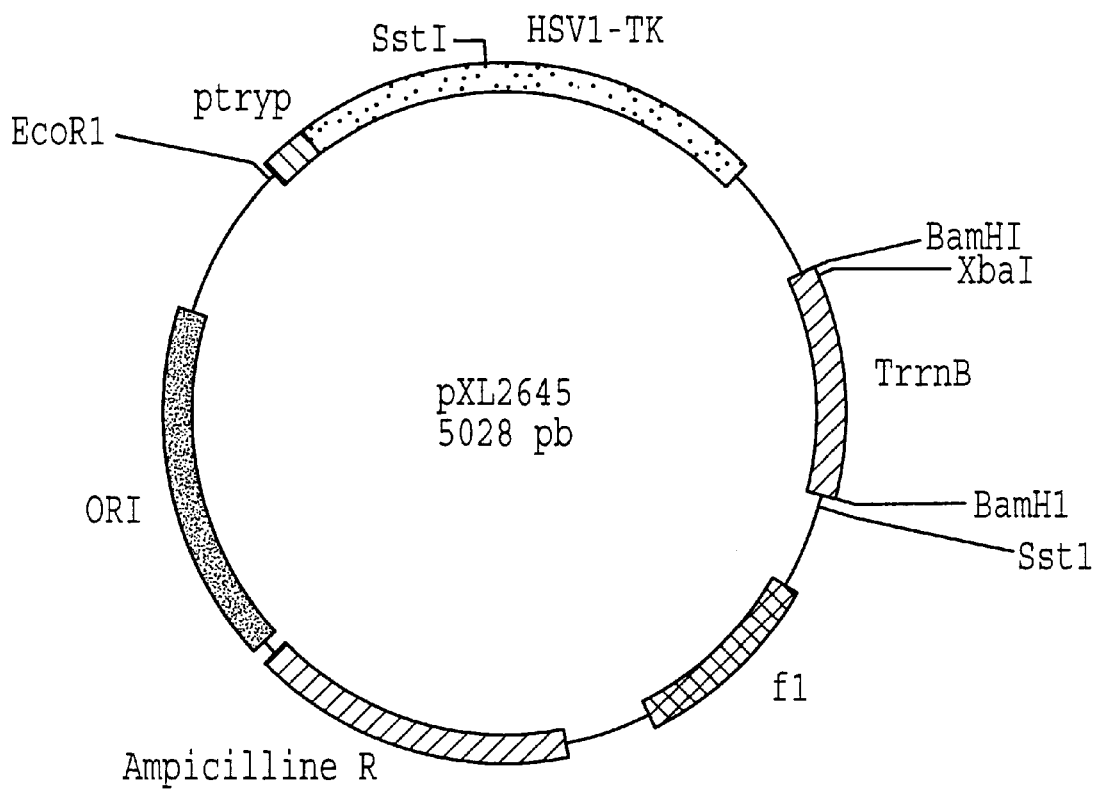

VARIANTS OF THYMIDINE KINASE, NUCLEIC ACIDS ENCODING THEM, AND METHODS OF USING THEM

The present invention relates to nucleic acid sequences coding for enzymes derived from the wild-type thymidine kinase, TK, enzyme, and possessing improved functions for the purpose of therapeutic use. It relates more especially to new enzymes possessing an improved substrate specificity and/or efficacy relative to the wild-type thymidine kinase enzyme. It also relates to vectors containing these nucleic acid sequences and to their therapeutic uses, in particular in gene therapy.

The present invention relates more especially to the field of gene therapy which employs suicide genes for the purpose of inducing the cell death of specific cells such as cells infected with a virus such as the HIV (human immunodeficiency virus), CMV (cytomegalovirus) or RSV (respiratory syncytial virus) type virus. This type of therapeutic treatment, consisting in causing a suicide gene to be expressed within a cell, is also applied for the treatment of cancers and of some cardiovascular diseases.

As suicide gene, it is preferable to use, in gene therapy, genes whose expression product endows the cell with a sensitivity to a therapeutic agent. More generally, the genes in question are ones that code for non-mammalian and non-toxic enzymes which, when they are expressed in mammalian cells, transform a prodrug which initially has little or no toxicity to a highly toxic agent. Such a mechanism of action of prodrugs is advantageous on several counts: it makes it possible to optimize the therapeutic index by adjusting the prodrug concentration or the expression of the enzyme, to interrupt the toxicity by no longer administering the prodrug, and to evaluate the mortality rate.

Numerous suicide genes are described in the literature, such as, for example, the genes coding for cytosine deaminase, purine nucleoside phosphorylase or a thymidine kinase such as, for example, the chickenpox virus or the herpes simplex virus type 1 thymidine kinases. Among these genes, the gene coding for herpes simplex virus type 1 thymidine kinase is most especially advantageous from a therapeutic standpoint since, in contrast to the other suicide genes, it generates an enzyme, thymidine kinase, capable of specifically eliminating dividing cells. This enzyme has a different substrate specificity from the cellular enzyme, and it has been shown to be the target of guanosine analogues such as acyclovir or ganciclovir (Moolten 1986 Cancer Res. 46, p. 5276).

In the particular case of the HSV1-TK/ganciclovir system, the mechanism of action may be outlined as follows: mammalian cells modified to express the HSV1-TK enzyme implement the first step of phosphorylation of ganciclovir to yield ganciclovir monophosphate. This step appears to be limiting. Subsequently, cellular kinases enable this ganciclovir monophosphate to be metabolized successively to diphosphate and then triphosphate. The ganciclovir triphosphate thus generated then produces toxic effects by becoming incorporated in the DNA, and partially inhibits the cellular DNA polymerase alpha, thereby causing DNA synthesis to be stopped and hence leading to cell death (Moolten 1986 Cancer Res. 46, p. 5276; Mullen 1994 Pharmac. Ther. 63, p. 199).

Moreover, a propagated toxicity effect ("bystander" effect) has been observed when TK is used. This effect manifests itself in the destruction not only of the cells which have incorporated the TK gene, but also the neighbouring cells. The mechanism of this process may be explained in three ways: i) the formation of apoptotic vesicles which contain thymidine kinase or phosphorylated ganciclovir, originating from dead cells, followed by phagocytosis of these vesicles by the neighbouring cells, ii) transfer of the prodrug metabolized by thymidine kinase, by a process of metabolic cooperation, from the cells containing the suicide gene to the cells not containing it, and/or iii) an immune response linked to regression of the tumour (Marini et al., 1995 Gene Therapy 2, p. 655).

For a person skilled in the art, the use of the suicide gene coding for herpesvirus thymidine kinase is very amply documented. In particular, the initial in vivo studies on rats having a glioma show regression of tumours when the HSV1-TK gene is expressed and when doses of 150 mg/kg of ganciclovir are injected (K. Culver et al., 1992 Science 256, p. 1550). However, these doses are highly toxic in mice (T. Osaki et al., 1994 Cancer Research 54, p. 5258) and hence totally banned in gene therapy in man.

A number of therapeutic trials are also in progress in man, in which the TK gene is delivered to the cells by means of different vectors such as, in particular, retroviral or adenoviral vectors. In clinical trials of gene therapy in man, the doses which have to be administered are much smaller, of the order of 5 mg/kg, and for a short treatment period (14 days) (E. Oldfield et al., 1995 Human Gene Therapy 6, p. 55). With higher doses or treatments over a longer period of time, adverse side effects are, in effect, observed.

It will hence be especially advantageous to have at one's disposal a suicide gene related to the gene coding for wild-type thymidine kinase, capable of generating a variant of the wild-type TK enzyme which would be more specific and/or more active in phosphorylating ganciclovir. Advantageously, such a variant may also be employed at a significantly reduced dose compared to the dose of wild-type suicide gene and, in addition, enable the dose of substrate which is traditionally combined with it to be reduced.

The objective of the present invention is, specifically, to provide a nucleic acid sequence coding for an enzyme of the thymidine kinase type having more potent activating behaviour in relation to ganciclovir or a nucleoside analogue.

The sequence of the gene coding for the herpes simplex virus type 1 thymidine kinase enzyme has been described in the literature (see, in particular, McKnight 1980 Nucl. Acids Res. 8, p. 5949). Natural variants of it exist, leading to proteins having a comparable enzyme activity with respect to thymidine, or ganciclovir (M. Michael et al., 1995 Biochem. Biophys. Res. Commun 209, p. 966). Similarly, derivatives have been described which were obtained by directed mutagenesis at the binding site of the enzyme with the substrate. However, no precise biochemical characterization has been carried out on the pure enzymes, and no cellular test using these mutants has been published (Black et al., 1993 Biochemistry 32, p. 11618). In addition, the inducible expression of an HSV1-TK gene from which its first 45 codons have been deleted has been carried out in eukaryotic cells, but the doses of prodrug used remain comparable to those described in all the trials in the literature (B. Salomon et al., 1995 Mol. Cell. Biol. 15, p. 5322). Consequently, none of the variants described hitherto displays improved activity in relation or with respect to ganciclovir.

The present invention describes the construction of new thymidine kinase variants possessing improved enzymatic properties. The present application also describes the construction of nucleic acid sequences coding for these variants, as well as vectors containing the said sequences and permitting their administration in vivo and the in vivo production of mutants.

Unexpectedly, the Applicant has, in effect, prepared, isolated and characterized a series of particular nucleic acid sequences coding for thymidine kinase variants possessing the requisite activating behaviour, that is to say significantly improved compared to that of wild-type thymidine kinase. The Applicant has, in particular, demonstrated that new thymidine kinase variants having improved enzyme properties could be obtained, in particular, by modification of the region of the protein responsible for the binding with ATP.

Thus, a first subject of the invention lies in a nucleic acid sequence coding for a thymidine kinase, characterized in that it possesses, in relation to the wild-type sequence, at least one mutation in the region corresponding to the ATP-binding site combined with at least one mutation in the N-terminal and/or C-terminal region.

More specifically, the first subject of the present invention is a nucleic acid sequence, characterized in that it is derived from the nucleic acid sequence coding for a wild-type thymidine kinase, the said nucleic acid sequence possessing at least one mutation in the region corresponding to the ATP-binding site and at least one mutation in the N-terminal and/or C-terminal region.

For the purposes of the present invention, the term mutation covers any substitution, deletion, addition and/or modification of one or more residues of the nucleic acid sequence in question. It is understood that the claimed nucleic acid sequence can comprise other mutations, localized or otherwise, in the regions as defined above.

According to a preferred embodiment of the invention, the nucleic acid sequence is derived from the sequence coding for herpes simplex virus type I TK. The mutation in the region corresponding to the ATP-binding site is preferably represented therein by at least one substitution of a guanine at position 180 by an adenine (G180A).

As regards the mutation present in the N-terminal portion of the TK, it may be a substitution of the guanine at position 16 by an adenine (G16A) or a double substitution of the guanines at position 28 and 30 by adenines (G28A and G30A).

According to a preferred embodiment of the invention, the claimed nucleic sequences carry, in addition to a mutation in the region corresponding to the ATP-binding site, at least one mutation in the C-terminal portion and more particularly localized between positions 990 and 1030. According to another embodiment of the invention, this mutation, which is present in the C-terminal portion, is in addition combined with at least one mutation localized in the N-terminal portion of the TK as defined above.

As representatives of such a sequence, there may be mentioned the nucleic acid sequences comprising at least one substitution of a guanine at position 180 by an adenine (G180A), at least one double substitution of the guanines at position 28 and 30 by adenines (G28A and G30A) a double substitution of the cystosines at position 591 and 892 by thymines (C591T and C892T) and a double substitution of the guanines at position 1010 and 1011 by adenines (G1010A and G1011A).

The nucleic acid sequence coding for a thymidine kinase variant is advantageously chosen from:
(a) the sequence SEQ ID No. 3 or a portion of the latter carrying the (G180A) mutation or one of their complementary strand,
(b) the sequences SEQ ID No. 6 and SEQ ID No. 7 or a portion of these sequences carrying the (G180A) mutation and, respectively, the G16A mutation and the (G28A; G30A) double mutation or one of their complementary strand, (c) the sequence SEQ ID No. 8 or a portion of the latter carrying the (G180A) mutation the (G28A; G30A) double mutation, and the (C591T; C892T; G1010A; G1011A) quadruple mutation or one of their complementary strand
(d) any sequence hybridizing with the sequences (a), (b) and/or (c) coding for a thymidine kinase variant and in accordance with the present invention,
(e) the variants of (a), (b), (c) and (d) resulting from the degeneracy of the genetic code.

The nucleic acid sequence according to the invention can be of eukaryotic, bacterial, viral, synthetic or semi-synthetic origin.

Generally, speaking, the nucleic acid sequences of the invention may be prepared according to any technique known to a person skilled in the art. By way of illustration of these techniques, there may be mentioned, in particular:
  chemical synthesis, using the sequences presented in the application and, for example, a nucleic acid synthesizer,
  the screening of libraries by means of specific probes, in particular such as are described in the application, or alternatively
  mixed techniques including chemical modification (elongation, deletion, substitution, and the like) of sequences screened from libraries.

The nucleic acid sequences according to the invention may also be obtained by mutagenesis, site-directed or otherwise, of a natural or already mutated nucleic acid sequence coding, respectively, for a wild-type thymidine kinase or one of its variants. Numerous methods enabling site-directed or random mutagenesis to be carried out are known to a person skilled in the art, and there may be mentioned site-directed mutagenesis using PCR or oligonucleotides, and random mutagenesis in vitro by chemical agents such as, for example, hydroylamine or in vivo in mutator strains of *E. coli* (Miller "A short course in bacterial genetics", Cold Spring Harbor Laboratory, Cold Spring Harbor, N.Y., 1992).

The present invention thus extends to any nucleic acid sequence coding for a variant of a wild-type thymidine kinase and capable of being obtained from a nucleic acid sequence as claimed by employing one of the modification techniques mentioned above, and more preferably mutagenesis, site-directed or otherwise.

Advantageously, the products of the claimed sequences according to the present invention prove more potent than the natural enzyme from which they are derived by structural modification(s). When expressed in target cells, they display an improved enzyme activity relative to the natural enzyme with respect to ganciclovir or a nucleoside analogue. The behaviour terms "more activating" or "improved enzyme activity" of the variants according to the invention is assessed by comparison to that of the wild-type enzyme, according to protocols described in detail in the examples below.

For the purposes of the present invention, nucleoside analogue is understood to cover compounds of the acyclovir, trifluorothymidine, 1-(2-deoxy-2-fluorobeta-D-arabinofuranosyl)-5-iodouracil, ara-A, araT, 1-beta-D-arabinofuranosylthymidine, 5-ethyl-2'-deoxyuridine, iodouridine, AZT, AIU, dideoxycytidine and AraC. By way of a preferred analogue in the context of the present invention, BVDU, ganciclovir and penciclovir may be mentioned more especially.

The subject of the present invention is also wild-type thymidine kinase variants capable of being expressed from a claimed nucleic acid sequence.

More especially, the invention extends to any variant of a thymidine kinase, characterized in that it comprises at least one mutation in its ATP-binding site combined with at least one mutation in the N-terminal and/or C-terminal region.

The localization of this ATP-binding site within the thymidine kinase peptide sequence varies according to the viral origin of the enzyme. Thus, depending on whether the thymidine kinase in question is from the chickenpox virus or from the herpes simplex virus, type 1 or otherwise, this region is positioned in different regions. However, generally speaking, it is present therein in the consensus GXXXXGK(T/S) (SEQ ID No. 1) with X representing any amino acid, and, in the particular case of herpes simplex virus type 1 thymidine kinase, in the following specific sequence: GPHGMGKT (SEQ ID No. 2).

Consequently, the present invention relates to any variant of a wild-type thymidine kinase in accordance with the invention and comprising at least one mutation in its following peptide region: GXXXXGK(T/S).

According to a preferred embodiment of the present invention, the sequence possessing at least one mutation is that represented by GPHGMGKT (SEQ ID No. 2). In this particular case, the mutation is more preferably represented therein by at least one substitution at position 60 of a methionine by an isoleucine.

As a representative of this type of mutant, the mutant 1537:E4 described in the examples below may be mentioned more especially.

As regards more especially the mutation in the N-terminal region. It is preferably localized in the amino acids numbered from 1 to 20. More preferably, the said mutation is localized in the amino acids numbered from 1 to 15. Still more preferably, the said mutation is localized in the amino acids numbered from 1 to 10. According to a preferred embodiment, the said mutation is localized in the amino acids numbered from 5 to 10.

According to a preferred embodiment, the present invention relates to a variant of herpes simplex virus type I thymidine kinase comprising at least one mutation represented by a substitution at position 60 of a methionine by an isoleucine and by a substitution at position 10 of an alanine by a threonine.

As a representative of this type of mutant, the mutant 2-865:H12 described in the examples below may be mentioned more especially.

According to another most especially preferred embodiment of the present invention, it is a variant of herpes simplex virus type I thymidine kinase comprising at least one mutation represented by a substitution at position 60 of a methionine an isoleucine and substitution at position 6 of a glycine by a serine.

As a representative of this type of mutant, the mutant 2-3361:D3 described in the examples below may be mentioned more especially.

As regards the mutation in the C-terminal region, it is preferably localized in the amino acids numbered from 320 to 350. More preferably, the said mutation is localized in the amino acids numbered from 325 to 345. Still more preferably, the said mutation is localized in the amino acids numbered from 330 to 343. According to a preferred embodiment, the said mutation is localized in the amino acids numbered from 335 to 340.

According to a most especially preferred embodiment of the present invention, it is a variant of herpes simplex virus type I thymidine kinase comprising at least one substitution at position 60 of a methionine by an isoleucine, a substitution at position 10 of an alanine by a threonine and a substitution at position 337 of an arginine by a glutamine.

As a representative of this type of mutant, the mutant 3-4216:H2 described in the examples below may be mentioned more especially.

Advantageously, the variants according to the invention display improved performance features in one or more of the following enzymatic characteristics:

inhibition by the substrate: inhibition by ganciclovir at high concentration is generally observed with the wild-type enzyme; it is decreased or even eliminated with the variants according to the invention.

Rate of phosphorylation of ganciclovir or of another nucleoside analogue: the variants according to the invention advantageously possess a higher rate of phosphorylation of ganciclovir or of another analogue;

Rate of phosphorylation of thymidine: it is preferably unchanged or decreased with the variants of the invention which confers on them greater selectivity in relation to ganciclovir or of the nucleoside analogue. This rate of phosphorylation of thymidine will be defined in the text which follows through its specificity constant Kcat/Km. This is a second-order apparent rate constant which is familiar to persons skilled in the art. It makes it possible to describe the properties and the reactions of the free enzyme and of the free substrate. For substrates in competition, it determines the specificity of the enzyme towards these substrates. (A. Fersht, Enzyme Structure and Mechanism 1985, W. H. Freeman, London).

Preferably, the variants according to the invention and particular the variant 1537:E4 advantageously manifest the following kinetic properties:

a substantial or even complete decrease in the inhibition of the activity of phosphorylation of ganciclovir contrary to the wild-type enzyme for which the inhibition is very marked at and above 15 $\mu$M;

an increase by at least a factor of 2 to 2.5 in the initial rate of phosphorylation of GCV at and above 15–20 $\mu$M, relative to the wild-type enzyme, and a Kcat/Km ratio for thymidine which is reduced by at least a factor of 1 to 6 relative to that of the wild-type enzyme, and preferably by at least 2.

Preferably, the variants according to the invention, and more particularly the variants 2-865:H12 and 2-3361:D3 display at least one of the following performance features:

a significant decrease in the inhibition of the phosphorylation of ganciclovir or of the nucleoside analogue at high concentrations of ganciclovir or of nucleoside analogue, a rate of phosphorylation of ganciclovir or of the nucleoside analogue which is at least tripled and/or a Kcat/Km ratio for thymidine which is either unchanged as for the mutant 2-865:H12 or reduced by a factor at least equal to 5 as for the mutant 2-3361:D3 relative to that of the wild-type enzyme.

More preferably, the variant 3-4216:H2 according to the invention displays at least one of the following kinetic performance features:

an absence of inhibition of the phosphorylation of ganciclovir or of the nucleoside analogue at high concentrations of ganciclovir or of nucleoside analogue, an increase by a factor greater than 3.5 in the initial rate of phosphorylation of GCV at and above 15–20 $\mu$M, relative to the wild-type enzyme and/or a Kcat/Km ratio for thymidine which is decreased by a factor of 4, relative to that of the wild-type enzyme.

From these data, it is apparent that the variant 3-4216:H2 manifests a particularly advantageous behaviour according to the invention.

Such qualities are especially advantageous from a therapeutic standpoint, since they make it possible to envisage a significant reduction in the doses at which enzymes and/or nucleoside analogue is/are used for an at least equivalent or even greater efficacy. Safety is enhanced without this having any detrimental effect on efficacy.

For the purposes of the invention, the term variant is also understood, according to the present invention, to denote any enzyme obtained by modification, using genetic engineering techniques, of the nucleic acid sequence coding for a wild-type thymidine kinase and possessing the behaviour defined above in relation to the ganciclovir and/or a nucleoside analogue. (Modification should be understood to mean any mutation, substitution, deletion, addition or modification of a genetic and/or chemical nature).

Naturally, these derivatives according to the invention, capable of inducing the destruction of the said cells via the activation of ganciclovir or one of its analogues, may advantageously be expressed in vivo directly from the claimed nucleic acid sequences.

To this end, the present invention also relates to any expression cassette comprising a nucleic acid sequence as defined above, a promoter permitting its expression and a transcription termination signal. The promoter is advantageously chosen from promoters which are functional in mammalian, preferably human, cells. More preferably, the promoter in question is one that permits the expression of a nucleic acid sequence in a hyperproliferative cell (cancer cell, restenosis, and the like). In this connection, different promoters may be used. A possible promoter is, for example, the one actually belonging to the herpes simplex type I TK gene. Sequences of different origin (responsible for the expression of other genes, or even synthetic sequences) are a, further possibility. Thus, it is possible to use any promoter or derived sequence that stimulates or represses the transcription of a gene, specifically or otherwise, inducibly or otherwise, strongly or weakly. The promoter sequences of eukaryotic or viral genes may be mentioned in particular. Possible promoter sequences are, for example, ones originating from the target cell. Among eukaryotic promoters, it is possible to use, in particular, ubiquitous promoters (promoter of the HPRT, PGK, alpha-actin, tubulin, DHFR, and the like, genes), promoters of intermediate filaments (promoter of the GFAP, desmin, vimentin, neurofilament, keratin, and the like, genes), promoters of therapeutic genes (for example the promoter of the MDR, CFTR, factor VIII, ApoAI, and the like, genes), tissue-specific promoters (promoter of the pyruvate kinase, villin, intestinal fatty acid binding protein, smooth muscle alpha-actin, and the like, gene), promoters of specific cells of the dividing cell type, such as cancer cells, or alternatively promoters that respond to a stimulus (steroid hormone receptor, retinoic acid receptor, glucocorticoid receptor, and the like) or so-called inducible promoters. Similarly, the promoter sequences may be ones originating from the genome of a virus, such as, for example, the promoters of the adenovirus E1A and MLP genes, the CMV early promoter or alternatively the RSV LTR promoter, and the like. In addition, these promoter regions may be modified by adding activating or regulatory sequences, or sequences permitting a tissue-specific or -preponderant expression.

The present invention now provides new therapeutic agents that make it possible to interfere with numerous types of cell dysfunction. To this end, the nucleic acids or cassettes according to the invention may be injected as they are at the site to be treated, or incubated directly with the cells to be destroyed or treated. It has, in effect, been reported that naked nucleic acid sequences could enter cells without a particular vector. Nevertheless, it is preferable in the context of the present invention to use an administration vector enabling (i) the efficacy of entry into the cell, (ii) targeting and (iii) extra- and intracellular stability to be improved.

In an especially preferred embodiment of the present invention, the nucleic acid sequence or cassette is incorporated in a vector. The vector used may be of chemical, biochemical or viral origin.

Chemical vector is understood to cover, for the purposes of the invention, any non-viral agent capable of promoting the transfer of nucleic acid sequences to eukaryotic cells and their expression therein. These synthetic or natural, chemical or biochemical vectors represent an advantageous alternative to natural viruses, especially for reasons of convenience and safety and also on account of the absence of theoretical limit regarding the size of the DNA to be transfected. These synthetic vectors have two main functions, to compact the nucleic acid which is to be transfected and to promote its binding to the cell as well as its passage through the plasma membrane and, where appropriate, both nuclear membranes. To compensate for the polyanionic nature of nucleic acids, non-viral vectors all possess polycationic charges. As representatives of this type of non-viral transfection techniques which are currently developed for the introduction of genetic information, there may thus be mentioned those involving complexes of DNA and DEAE-dextran (Pagano et al., J. Virol.1 (1967) 891), of DNA and nuclear proteins (Kaneda et al., Science 243 (1989) 375) and of DNA and lipids (Felgner et al., PNAS 84 (1987) 7413), the use of liposomes (Fraley et al., J. Biol. Chem. 255 (1980) 10431), and the like.

More recently, the use of viruses as vectors for gene transfer has been seen to be a promising alternative to these physical transfection techniques. In this connection, different viruses have been tested for their capacity to infect certain cell populations. This applies especially to retroviruses (RSV, HMS, MMS, and the like), the HSV virus, adeno-associated viruses and adenoviruses.

The nucleic acid sequence or vector used in the present invention may be formulated for the purpose of topical, oral, parenteral, intranasal, intravenous, intramuscular, subcutaneous, intraocular, transdermal, and the like, administration. Preferably, the nucleic acid sequence or vector is used in an injectable form. It may hence be mixed with any pharmaceutically acceptable vehicle for an injectable formulation, in particular for direct injection at the site to be treated. Possible formulations include, in particular, sterile isotonic solutions, and dry, in particular lyophilized compositions which, on addition of sterilized water or of physiological saline as appropriate, enable injectable solutions to be made up. A direct injection of the nucleic acid sequence into the patient's tumour is advantageous, since it enables the therapeutic effect to be concentrated in the affected tissues. The doses of nucleic acid sequences used may be adapted in accordance with various parameters, and in particular in accordance with the vector, the mode of administration used, the pathology in question or the desired treatment period.

The invention also relates to any pharmaceutical composition comprising at least one nucleic acid sequence as defined above.

It also relates to any pharmaceutical composition comprising at least one vector as defined above.

It also relates to any pharmaceutical composition comprising at least one thymidine kinase variant as defined above.

As a result of their antiproliferative properties, the pharmaceutical compositions according to the invention are most especially well suited to the treatment of hyperproliferative disorders such as, in particular, cancer and restenosis. The present invention thus provides an especially effective method for the destruction of cells, in particular hyperproliferative cells. It is thus applicable to the destruction of tumour cells or vascular wall smooth muscle cells (restenosis). It is most especially suitable for the treatment of cancer. As an example, there may be mentioned adenocarcinoma of the colon, thyroid cancer, carcinoma of the lung, myeloid leukaemia, colorectal cancer, breast cancer, lung cancer, stomach cancer, cancer of the oesophagus, B lymphoma, ovarian cancer, bladder cancer, glioblastoma, hepatocarcinoma, bone cancer, skin cancer, cancer of the pancreas or kidney and prostate cancer, cancer of the larynx, cancer of the head and neck, HPV-positive anogenital cancer, EBV-positive cancer of the nasopharynx, and the like.

It may be used in vitro or ex vivo. Ex vivo, it consists essentially in incubating the cells in the presence of a nucleic acid sequence (or of a vector or cassette or of the derivative directly). In vivo, it consists in administering to the body an active amount of a vector (or of a cassette) according to the invention, preferably directly at the site to be treated (tumour in particular), prior to, simultaneously with and/or after injection of the prodrug in question, that is to say ganciclovir or a nucleoside analogue. In this connection, the subject of the invention is also a method of destruction of hyperproliferative cells, comprising the bringing of the said cells or of a portion of them into contact with a nucleic acid sequence or a thymidine kinase variant as are defined above.

Consequently, the present invention provides a TK enzyme mutated in such a way that the phosphorylation of ganciclovir or of the nucleoside analogue employed is very significantly increased. Advantageously, it is thus possible, according to the invention, to use in cellular and clinical tests a mutated TK nucleic acid sequence at doses of prodrug i) which are significantly lower, ii) or are capable of causing a more pronounced "bystander" effect, iii) or alternatively which do not lead to a cellular toxicity which could occur when wild-type thymidine kinase is overexpressed.

The present invention will be described more fully by means of the examples and figures which follow, which are to be considered to be illustrative and non-limiting.

LEGEND TO THE FIGURES

FIG. 1: Expression plasmid pXL2645

Figure 2:
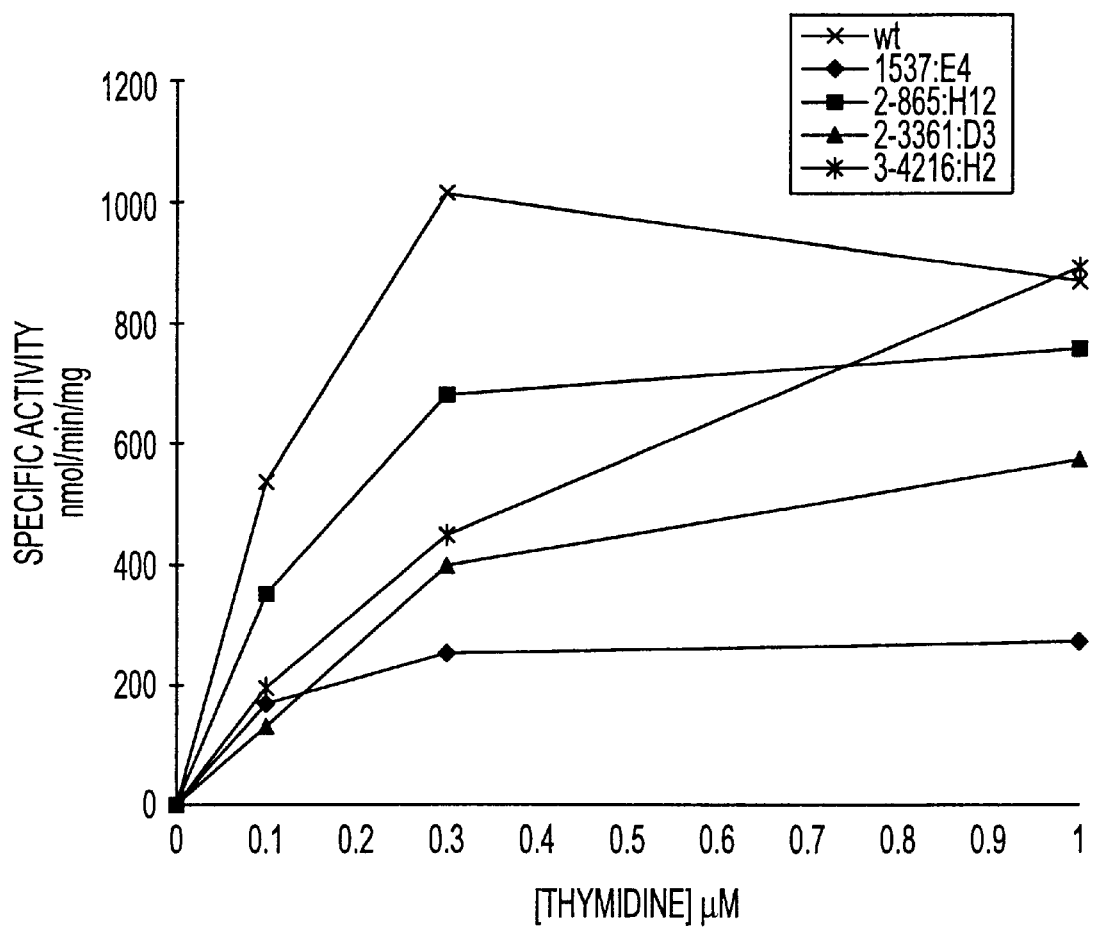

FIG. 2: Initial rates of phosphorylation (specific activity in nmol/min/mg) as a function of the thymidine concentration ($\mu$M) for the wild-type and mutant 1537:E4, 2-865:H12, 2-3361:D3 and 3-4216:H2 HSV1-TK enzymes FIG. 3: The curves represent the rates of phosphorylation (specific activity in nmol/min/mg) as a function of the ganciclovir concentration in $\mu$M for the wild-type and mutant (1537:E4, 2-865:H12, 2-3361:D3 and 3-4216:H2) HSV1-TK enzymes.

Figure 4:
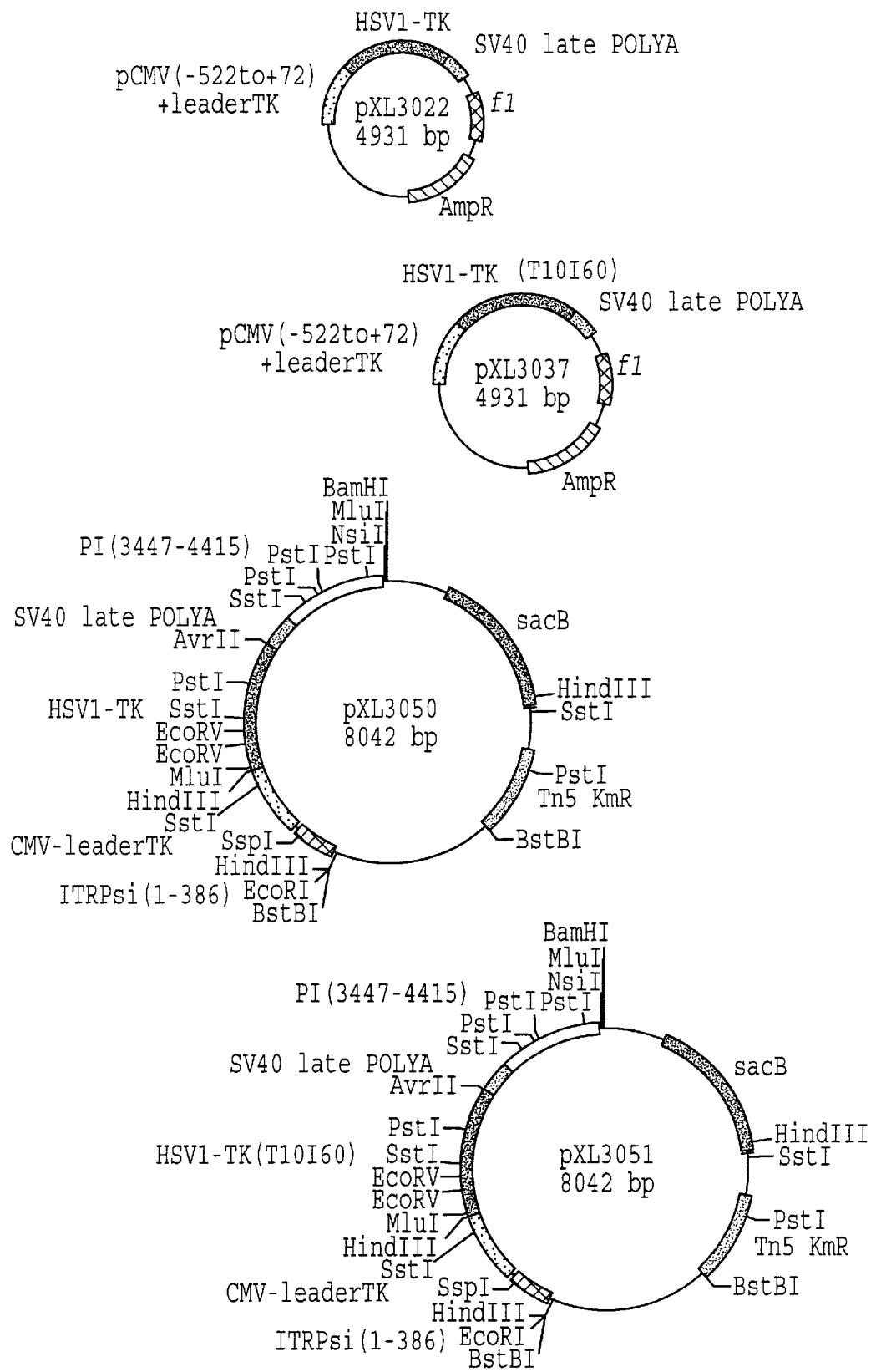

FIG. 4: Diagrammatic representation of plasmids pcDNA3-TK, pXL 3022 and pXL3037. Table I below summarizes the kinetic constants of these enzymes with respect to ganciclovir and thymidine.

TABLE 1

| Thymidine kinase | Thymidine | | | Ganciclovir | | Acyclovir | |
|---|---|---|---|---|---|---|---|
| | $K_m$ ($\mu$M) | $V_{max}$ nmol/min/mg | Kcat/Km $s^{-1}/\mu M^{-1}$ | $S_{0.5}$ ($\mu$M) | Vmax obs nmol/min/mg | $S_{0.5}$ ($\mu$M) | Vmax obs |
| Wild-type | 0.12 ± 0.02 | 1020 ± 105 | 3540 | 4.13 | 400 | 51 | 220 |
| 1537:E4 | 0.07 ± 0.01 | 305 ± 12 | 1815 | 6.4 | 550 | 66 | 250 |
| 2-865:H12 | 0.12 ± 0.04 | 880 ± 77 | 3055 | 6.15 | 1080 | 62 | 280 |
| 2-3361:D3 | 0.47 ± 0.12 | 718 ± 85 | 637 | 5.77 | 730 | 45 | 220 |
| 3-4216:H2 | 0.71 ± 0.05 | 1486 ± 37 | 870 | 14.3 | 2100 | 123 | 590 |
| | | | | Km 24.3 ± 3.8 | Vmax 2800 ± 130 | 255 ± 16 | 910 ± 28 |

Given that GCV does not display conventional Michaelis kinetic constants (except with the mutant 3-4216:H2), the values are expressed with the aid of S0.5 (i.e. substrate concentration leading to half the maximum speed observed).

MATERIALS AND METHODS

Abbreviations

ACV: acyclovir

GCV: ganciclovir

HSV1-TK: herpes simplex virus type 1 thymidine kinase

General techniques of molecular biology

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol/chloroform extraction of proteins, ethanol or isopropanol precipitation of DNA in a saline medium and transformation in *Escherichia coli*, are well known to a person skilled in the art and are amply described in the literature (Sambrook et al., "Molecular Cloning, a Laboratory Manual", Cold Spring Harbor Laboratory, Cold Spring Harbor, N.Y. 1989; Ausubel et al., "Current Protocols in Molecular Biology", John Wiley & Sons, New York, 1987).

Plasmids of the pUC type and phages of the M13 series are of commercial origin (Bethesda Research Laboratories); pBSK or PBKS plasmids are obtained from Stratagen.

The enzymatic amplification of DNA fragments by the so-called PCR (polymerase-catalyzed chain reaction) technique may be performed using a "DNA thermal cycler" (Perkin Elmer Cetus) according to the manufacturer's recommendations.

The electroporation of plasmid DNA into *E. coli* cells maybe carried out using an electroporator (Bio-Rad) according to the supplier's recommendations.

Verification of the nucleotide sequences may be performed by the method developed by Sanger et al. [Proc. Natl. Acad. Sci. USA, 74 (1977) 5463–5467] using the kit distributed by Amersham or the one distributed by Applied Biosystems.

EXAMPLE 1

BIOCHEMICAL SCREENING OF HSV1-TK MUTANTS 1-1 Plasmid for the Prokaryotic Expression of the HSV1-TK Gene Several systems for the expression of the HSV1-TK gene in E. coli are described in the literature (Colbère et al., 1979 Proc. Natl. Acad. Sci. USA 76 p. 3755; Kit et al., 1981 Gene 16 p. 287; Waldman et al., 1983 J. Biol. Chem. 258 p. 11571; Fetzer et al., 1992 Pharm. Pharmacol. Lett. 2 p. 112; Brown et al., 1995 Nature Structural Biology 2 p. 876). The one which is described below permits a very well regulated and high production of the HSV1-TK protein in its native (unfused, non-truncated) form.

The prokaryotic expression plasmid pXL2638 was constructed from the plasmid pHSV-106 (Gibco-BRL) and the expression vector pET11a (obtained from Novagen) in the following manner. After the ends were blunted, the 1.5-kb BqlII-NcoI insert originating from pHSV-106 and containing the HSV1-TK gene, the sequence of which is published by McKnight 1980 Nucl. Acids Res. 8 p. 5949, was cloned at the SmaI site of pBSK to form the plasmid pBTK1. An NdeI site was introduced by site-directed mutagenesis starting from position −3 of the coding sequence of the HSV1-TK gene. For this purpose, a 500-bp fragment containing the 5' portion of the gene was amplified by PCR using pBTK1 as template and the sense oligonucleotide 5' (TTA TGA ATT CAT ATG GCT TCG TAC CCC GGC)3' SEQ ID No. 4 and the antisense oligonucleotide 5' (TTA TTT CTA GAG GTC GAA GAT GAG GGT)3' SEQ ID No. 5 as primers; this fragment was cloned into M13mp19 and then sequenced. This fragment, digested with EcoRI and SstI, generates a 460-bp insert which was cocloned with the 1-kb SstI-XbaI insert from pBTK1 containing the 3' portion of the HSV1-TK gene into plasmid pUC19 digested with EcoRI and XbaI; this plasmid pUCTK contains the HSV1-TK gene in the form of an NdeI-BamHI set, which was cloned between the NdeI and BamHI sites of pET11a to create plasmid pXL2638. This plasmid enables the HSV1-TK gene to be expressed under the control of the promoter of gene 10 of bacteriophage T7; this promoter being induced when the RNA polymerase of bacteriophage T7 is synthesized, as, for example, in E. coli strain BL21, lambdaDE3 (Studier et al., 1990 Methods Enzymol. 185 p. 89).

1-2 Preparation of Acellular Extracts

Acellular extracts of E. coli strain overproducing the HSV1-TK protein may be prepared in various ways, among which lysis with lysozyme in the presence of EDTA, the use of Menton-Golin, French Press or X-Press type grinding apparatuses or the action of ultrasound may be mentioned. More especially, the acellular extracts of E. coli strain BL21, lambdaDE3 (Novagen Inc) pXL2638 were prepared in the following manner:

E. coli strain BL21, lambdaDE3 pXL2638 is cultured in LB (Luria-Bertani) medium+ampicillin (50 mg/l) at 37° C. to an absorbance at 600 nm of 0.7; production of the HSV1-TK protein is induced by adding 1 mM IPTG (isopropyl beta-D-thiogalactoside), and takes place on continuing the growth of the cells for 3 hours at 30° C. After centrifugation (5000×g; 20 min), the cells obtained from 1 l of culture are resuspended in 10 ml of 50 mM Tris-HCl buffer pH 7.8 containing 5 mM DTT, 4 mM MgCl$_2$ and 10% glycerol (v/v), and sonicated for 4 min at 4° C. After centrifugation (50,000×g; 1 h), the supernatant is injected onto a column of Source 15Q (50 ml of gel, Pharmacia) equilibrated in the above buffer. The proteins are eluted with a linear gradient of 0 to 400 mM NaCl in buffer A. The fractions containing the TK activity are pooled, taken to a final concentration of 1,1 M ammonium sulphate and chromatographed on a column of Phenyl-Superose HR 10/10 (Pharmacia) eluted with a linear gradient decreasing from 1.1 to 0 M ammonium sulphate. The fractions containing the TK activity are pooled. After this step, the preparation displays a single band visible in SDS-PAGE after visualization with Coomassie blue, and this band migrates with an apparent molecular weight of approximately 41,000.

1-3 Assay of TK Activity

The ATP-dependent activity of phosphorylation of nucleosides may be detected by proceeding, for example, in the following manner:

An enzyme extract containing approximately 0.1 unit of TK is incubated for 15 min at 37° C. in 100 $\mu$l of 50 mM Tris-HCl buffer pH 7.8 containing 1 mg/ml BSA (bovine serum albumin), 5 mM ATP, 4 mM MgCl$_2$, 12 mM KCl, 2 mM DTT, 600 $\mu$M EDTA and 100 $\mu$M [8-$^3$H]GCV (40 nCi/nmol). The reaction is stopped by adding 10 $\mu$l of 50 mM Tris-HCl buffer pH 7.8 containing 1 mM non-radioactive thymidine. The phosphorylated species are bound to a column of DEAE-Sephadex (400 $\mu$l of gel) and then, after the column is washed, these species are eluted with 2 ml of 1 M HCl. The radioactivity in the sample is then counted by liquid scintillation.

The assay of TK activity using thymidine as substrate is performed in the same manner, employing 0.002 unit of TK and 1 $\mu$M (methyl-$^{14}$C)thymidine (56nCi/nmol).

The unit of TK activity is defined as the amount of enzyme required to phosphorylate 1 nmol of substrate per min under the above conditions.

For the calculation of the kinetic constants, the amount of TK introduced into the enzyme reaction is adjusted so as to convert not more than 5% of the substrate introduced at the start, and the specific activity of this substrate is increased accordingly. The Michaelis curves are adjusted to the experimental points using the Enzfitter software (Sigma).

Since GCV does not display conventional Michaelis kinetic constants (except with the mutant 3-4216:H2), the values are expressed with the aid of S0.5 (i.e. substrate concentration leading to half the maximum speed observed)

1-4 Plasmid pXL2645 Permitting a Biochemical Screening

The heterologous expression systems in E. coli are many and well known to a person skilled in the art. Expression of the HSV1-TK gene proved to be the best one for biochemical screening when the gene is expressed using the tryptophan promoter pTryp at a high copy number on plasmid pXL2645. The 1.4-kb NdeI-XbaI insert from pUCTK is cocloned with the 120-bp NdeI-EcoRI and 3.1-kb EcoRI-XbaRI inserts from pXL694 (Jung et al., 1988 Ann. Inst. Pasteur/Microbiol. 139 p. 129) to generate the plasmid pXL2619. The following inserts from pXL2619, namely the 1.5-kb EcoRI-XbaI insert (containing the HSV1-TK gene and pTryp: the promoter/operator region of the E. coli tryptophan operon followed by the RBS (ribosome binding site) of the lambda cII gene) and 530-bp XbaI-BamHI insert containing the T$_{rrnB}$ terminator region of the E. coli ribosomal operon, are cocloned into the vector pBSK+to create plasmid pXL2645.

1-5 Mutagenesis of the Plasmid

Numerous methods enabling site-directed or random mutagenesis to be carried out on plasmids are known to a person skilled in the art, and there may be mentioned site-directed mutagenesis using PCR or oligonucleotides according to the recommendations of the supplier, Amersham, and random mutagenesis in vitro by chemical agents or in vivo in mutator strains of E. coli (Miller "A short course in bacterial genetics", Cold Spring Harbor Laboratory, Cold Spring Harbor, N.Y., 1992). Plasmid pXL2645 was mutagenized with hydroxylamine according to a protocol already described and which leads to GC to AT transitions at random on the plasmid (Humphreys et al., 1976 Mol. Gen. Genet. 145 p. 101). Five μg of plasmid DNA dissolved in 0.2 M phosphate buffer pH 6 containing 0.4 M hydroxylamine, are incubated at 80° C. or 86° C. for 30 min and then cooled to room temperature for 20 min; the solution is thereafter dialyzed and then precipitated. The DNA is then redissolved in 50 μl of water. If the plasmid DNA is pCH110 (obtained from Pharmacia and carrying the lacZ gene), lacZ$^-$ mutants are obtained as a frequency of 2.4% (or 7.6%, respectively) when the plasmid is heated to 80° C. (or 86° C., respectively) in the presence of hydroxylamine.

1-6 Screening of Mutants Possessing a Modified TK

Plasmid pXL2645 mutagenized with hydroxylamine at 80° C. is introduced by electroporation into the E. coli tk$^-$ strain ME8025 (obtained from the National Institute of Genetics, Mishima, Shizuoka, Ken, Japan). The electroporants are inoculated individually into, the wells of a microtitration plate containing 100 μl of M9 minimum medium supplemented with 0.4% of casamino acids and 50 mg/l of ampicillin. The cultures are incubated at 37° C. with agitation for 17 hours. Fifteen μl of the culture diluted to ⅕s in 50 mM Tris-HCl buffer pH 7.8 are incubated for 20 min at 37° C. in a volume of 250 μl of 50 mM Tris-HCl buffer pH 7.8 containing 2 mg/ml of egg white lysozyme, 5 mM ATP, 4 mM MgCl$_2$, 12 mM KCl, 2 mM DTT, 600 μM EDTA, 16 μM [-$^3$H]GCV (60 nCi/nmol) and 1 μM [methyl-$^{14}$C] thymidine (56 nCi/nmol). The reaction is stopped by adding 25 μl of 50 mM Tris-HCl pH 7.8 buffer containing 1 mM non-radioactive thymidine. The phosphorylated species are bound to a column of DEAE-Sephadex (400 μl of gel) and then, after the column is washed, these species are eluted with 2 ml of 1 M HCl. The radioactivity ($^3$H and $^{14}$C) in the sample is then counted by liquid scintillation using a double-labelling programme, and the $^3$H/$^{14}$C ratio is calculated for each sample.

For each 96-well microtitration plate, the mean of the $^3$H/$^{14}$C ratios of all of the clones (M) and the standard deviation (σ) of the distribution of the $^3$H/$^{14}$C ratios are calculated. Furthermore, the amount of proteins present in each of the wells of the 96-well plate is measured using Bradford's reagent (Coomassie Plus Protein Assay Reagent, Pierce) from an aliquot fraction of the ⅕s dilution prepared above. Any clone possessing a protein content less than one quarter of the mean of the clones of the dish is permanently discarded.

The $^3$H/$^{14}$ ratio obtained for each clone of a 96-well dish is compared with the mean M. Clones possessing a ratio higher than the sum M+3σ while displaying thymidine phosphorylation activity greater than M'/2,M' being the mean of the thymidine phosphorylation activities, are selected for confirmation and study.

Table 2 summarizes the results obtained after screening of 4129 clones originating from hydroxylamine mutagenesis of pXL2645 at 80° C. In this screening, for the wild-type enzyme, the TK activity is designated 100% and the GCV/Thy ratio is 1.

At the end of this study, a mutant termed 1537:E4 manifesting more activating behaviour with respect to ganciclovir is revealed.

TABLE 2

| TK activity | % < TK < % | Number | Names of mutants | Frequency % |
|---|---|---|---|---|
| High | 233 < TK < 320 | 2 | 3841:D2 3841:F3 | 0.05 |
| Low | 5 < TK < 10 | 17 | | 0.4 |
| Zero | TK < 5 | 99 | | 2.4 |
| Zero with respect to GCV but unchanged with respect to thymidine | | 1 | 2881:C8 | 0.02 |
| High with respect to GCV but unchanged with respect to thymidine | GCV/Thy: 1.76 (σ:0.11) 1.70 (σ:0.19) | 2 | 1537:E4 1921H:12 | 0.05 |

EXAMPLE 2

PRIMARY STRUCTURE AND BIOCHEMICAL CHARACTERIZATION OF THE MUTANT 1537:E4

2-1 Sequence of the HSV1-TK Gene of the Mutant 1537:E4

The HSV-TK gene expressed from the mutant 1537:E4 was sequenced on both strands and a single G180A mutation was observed. This mutation corresponds to a Met60Ile substitution. It should be noted that this residue is located in the consensus region of the ATP-binding site. A comparable study was carried out with the mutant 1921:H12 and the same substitution (Met60Ile) was observed.

2-2 Cloninq of the HSV1-TK Gene of the Mutant 1537:E4 Into a High Expression Prokarvotic Vector The 1.4-kb NdeI-BamHI insert coding for the HSV1-TK gene of the mutant 1537:E4 was cloned into the expression vector pET11a to generate pET:E4. This plasmid pET:E4 is the one from which the HSV1-TK enzyme of the mutant 1537:E4 was produced in E. coli BL21, lambdaDE3 under the conditions described in 1-2.

2-3 Biochemical Data

The kinetic constants for the mutant 1537:E4 TK and the wild-type TK taken as reference are obtained under the enzyme assay conditions described in Section 1-3.

The 2 TKs (wild-type and mutant 1537:E4) do not display a Michaelis behaviour with ganciclovir and acyclovir (inhibition at high concentration). This therefore prohibits the calculation of a Km value with these 2 substrates. There maybe given only the $S_{0.5}$ concentration corresponding to the substrate concentration giving an initial speed equal to half the maximum speed observed. Vmax and Vmax obs are expressed therein in nmol/min/mg of protein.

The curve in FIG. 2 shows the initial rates of phosphorylation as a function of the GCV concentration for both 1537:E4 and wild-type enzymes. It brings out, in particular, the almost complete absence of inhibition of the activity of phosphorylation of GCV by the mutant 1537:E4 TK, contrary to the wild-type enzyme for which inhibition is very marked at and above 15 μM. This curve shows, furthermore, an increase by a factor of 2 to 2.5 in the initial rate of phosphorylation of GCV at and above 15–20 μM with the mutant 1537:E4 enzyme, relative to the wild-type enzyme. The mutant enzyme 1537:E4 displays therein a Kcat/Km ratio for thymidine which is reduced by a factor of 2 relative to the wild-type enzyme.

EXAMPLE 3

OBTAINING, PRIMARY STRUCTURE AND BIOCHEMICAL CHARACTERIZATION OF THE MUTANTS 2-865:H12 AND 2-3361:D3

3-1 Obtaining the Mutants 2-856:H12 and 2-3361:D3

The plasmid pXL2838 originating from the mutant 1537:E4 carries, under the control of the pTryp promoter, the HSV1-TK gene whose TK protein differs from the wild-type protein by the mutation M60I. This plasmid is mutagenized with hydroxylamine at 86° C. and then introduced by electroporation into the E. coli tk⁻ strain ME8025. A total of 4992 electroporants are analyzed for their capacity to phosphorylate ganciclovir and thymidine as described in Example 1-6. The results of this screening are summarized in Table 3, where the TK activity is designated 100% and the GCV/Thy ratio is 1 for the wild-type enzyme. Two mutants, 2-865:H12 and 2-3361:D3, display more activating behaviour with respect to ganciclovir.

TABLE 3

| TK activity | % < TK < % | Number | Names of mutants | Frequency % |
|---|---|---|---|---|
| Zero | TK < 5 | 227 | | 4.5 |
| Low | 5 < TK < 10 | 55 | | 1.1 |
| High with respect to GCV but unchanged with respect to thymidine | GCV/Thy: 4.95+/−0.66 3.99+/−0.53 | 2 | 2-865:H12 2-3361:D3 | 0.04 |

3-2 Sequence of the HSV1-TK Gene of the Mutants 2-865:H12 and 2-3361:D3

The HSV1-TK gene expressed from the mutants 2-865:H12 and 2-3361:D3 was sequenced on both strands and the following mutations were observed. With the mutant 2-865:H12, the mutations are G28A, G30A and G180A, corresponding to the substitutions Ala10Thr and Met60Ile. Whereas with the mutant 2-3361:D3, the mutations are G16A, G180A, C306T and C308T, corresponding to the substitutions Gly6Ser, Met60Ile and Thr103Ile.

3-3 Importance of the Mutation Localized in the N-terminal Region of the TK

The enzymes of the mutants 2-865:H12 and 2-3361:D3 both carry a mutation in the N-terminal portion of the thymidine kinase, position 10 or 6. Since the enzyme corresponding to the mutant 2-3361:D3 also contains a mutation at position 103, plasmids containing the mutations at positions 6 and 60 (pXL2964) or at positions 60 and 103 (pXL2963) or at position 103 (pXL2965) or at position 6 only (pXL2966) were constructed in the following manner: the 400-bp SnaBI-BspEI insert from the plasmid pXL2840 (plasmid extracted from the mutant 2-3361:D3) was cloned either into plasmid pXL2645 digested with SnaBI-BspEI to generate pXL2965, or into plasmid pXL2838 digested with SnaBI-BsPEI to generate pXL2963. Plasmid pXL2964 corresponds to the ligation of the 2.9-kb MluI-XmnI insert from pXL2838 with the 2.1-kb XmnI-MluI fragment of pXL2840. The plasmid pXL2966 corresponds to the ligation of the 2.9 kb MluI-XmnI insert from pXL2645 with the 2.1 kb XmnI-MluI fragment of pXL2840. These plasmids were transformed into E. coli strain ME8025, and the thymidine kinase activity with respect to thymidine and ganciclovir is determined as in Example 1-6; the GCV/Thy ratios are seen in Table 4.

TABLE 4

| Plasmid (Mutant) | Mutation of the TK enzyme | GCV/Thy |
|---|---|---|
| pXL2645 | Wild-type TK | 1.00+/−0.08 |
| pXL2838 (1537:E4) | M60I | 1.60+/−0.17 |
| pXL2840 (2-3361:D3) | G6S, M60I, T103I | 3.10+/−0.26 |
| pXL2963 | M60I, T103I | 1.60/−0.18 |
| pXL2964 | G6S, M60I | 2.80+/−0.40 |
| pXL2965 | T103I | 1.00+/−0.18 |
| pXL2966 | G6S | 1.40+/−0.20 |

Only the GCV/Thy ratio obtained with plasmid pXL2964 is comparable to that obtained with plasmid pXL2840. And the results collectively show that the mutation at position 6, not the mutation at position 103, is the one which leads to an improvement in the TK activity with respect to GCV of the mutant 2-3361:D3 relative to the mutant 1537:E4. Moreover, the mutation at position 6 alone leads to an improvement in the TK activity. The effect of this mutation is therefore additive to the effect of the mutation at position 60 for improving the TK activity with respect to GCV. Furthermore, the improvement obtained by combining these two mutations Gly6Ser and Met60Ile can also be obtained by combining with the mutation Met60Ile another mutation situated in the N-terminal portion of the thymidine kinase, for example the mutation Ala 10Thr.

3-4 Cloning of the HSV1-TK Gene of the Mutants 2-865:H12 and 2-3361:D3 Into a High Expression Prokaryotic Vector The NdeI-BamHI insert coding for the HSV1-TK gene originating from the mutant 2-865:H12 (or 2-3361:D3, respectively) was cloned into the expression vector pET11a to form the plasmid pXL2843 (or pXL2841, respectively). These plasmids were transformed into E. coli BL21met⁻ lambdaDE3 in order to produce the enzymes of these two mutants.

3-5 Biochemical Data

Figure 3:
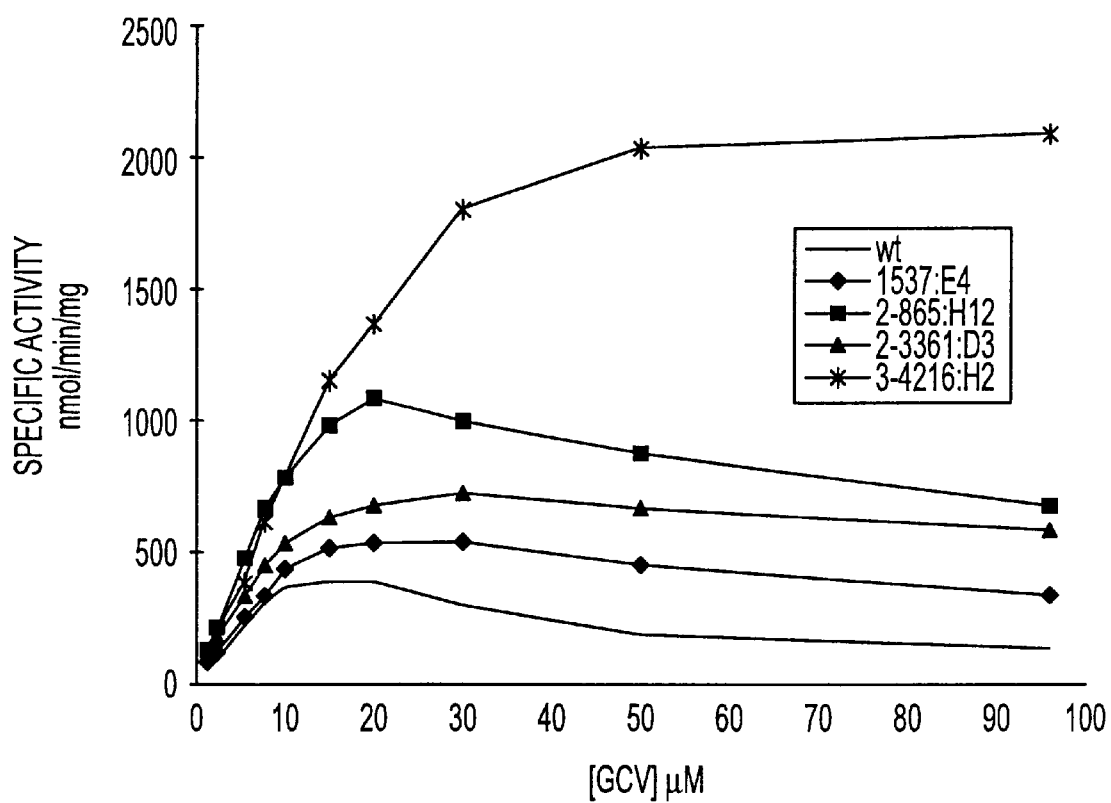

The TK enzymes originating from the E. coli BL21met⁻ lambdaDE3, pXL2843 and E. coli BL21 met⁻ lambdaDE3, pXL2841 cultures were purified to homogeneity. The kinetic constants for the TK of the mutants 2-865:H12 and 2-3361:D3 were determined and compared with those of the wild-type and the mutant 1537:E4 TK. The set of values is recorded in FIG. 3. The curves in FIG. 3 show the rates of phosphorylation as a function of the GCV concentration for the four enzymes. They bring out a partial lifting of the inhibition by GCV of the mutant 1537:E4, 2-865:H12 and 2-3361:D3 TKs, contrary to the wild-type enzyme for which inhibition is marked above 30 μM. These curves also show an increase in the rate of phosphorylation of GCV by a factor of 1.6 to 2.5 at 16 μM GCV and of 4.3 to 4.9 at 100 μM GCV, relative to the wild-type enzyme. Table 1 of FIG. 3 shows that the enzyme of the mutant 2-865:H12 possesses a Kcat/Km ratio for thymidine which is unchanged relative to that of the wild-type enzyme, and that of the mutant 2-3361:D3 manifests a Kcat/Km ratio which is reduced by a factor greater than or equal to 5 relative to that of the wild-type enzyme.

EXAMPLE 4

OBTAINING, PRIMARY STRUCTURE OF THE MUTANT AND BIOCHEMICAL CHARACTERIZATION OF THE MUTANT 3-4216:H2

4.1 Obtaining of the Mutant 3-4216:H2

The plasmid pXL2842 originating from the mutant 2-865:H12 carries, under the control of the pTryp promoter, the HSV1-TK gene whose TK protein differs from the wild-type protein by the mutations Ala10Thr and Met60Ile. This plasmid is mutagenized with hydroxylamine at 86° C. and then introduced by electroporation into the E. coli tk⁻ strain ME8025. A total of 3900 electroporants are analysed for their capacity to phosphorylate ganciclovir and thymidine as described in Example 1-6. The results of this screening are summarized in Table 5, where the TK activity is designated 100% and the GCV/Thy ratio is 1 for the wild-type enzyme. A mutant 3-4216:H2 displays a more activating behaviour with respect to ganciclovir.

TABLE 5

| TK activity | % < TK < % | Number | Names of mutants | Frequency % |
|---|---|---|---|---|
| Zero | TK < 5 | 121 | | 3.2 |
| Low | 5 < TK < 10 | 19 | | 0.5 |
| Zero with respect to GCV but unchanged with respect to thymidine | | 1 | 3-2293:C4 | 0.025 |
| High with respect to GCV but unchanged with respect to thymidine | GCV/THy: 7.84+/−1.09 | 1 | 3-4216:H2 | 0.025 |

4.2 Sequence of the HSV1-TK Gene of the Mutant 3-4216:H2

The HSV1-TK gene expressed from the mutant 3-4216:H2 was sequenced on both strands and the following mutations were observed (G28A, G30A, G180A, C591T, C892T, G1010A and G1011A). These mutations correspond to the substitutions Ala10Thr, Met60Ile and Arg337Gln.

4-3 Cloning of the HSVI-TK Gene of the Mutant 3-4216:H2 Into a High Expression Prokaryotic Vector.

The NdeI-BamHI insert coding for the HSV1-TK gene originating from the mutant 3-4216:H2 was cloned into the expression vector pET11a to form the plasmid pXL3129. This plasmid was transformed into E. coli BL21met⁻ lambdaDE3 in order to produce the enzyme of this mutant.

4-4 Biochemical Data.

The TK enzyme originating from the E. coli BL21met⁻ lambdaDE3, pXL3129 was purified to homogeneity. The kinetic constants for the TK of the mutant 3-4216:H2 were determined and compared with those of the wild-type and mutant 1537:E4, 2-865:H12 and 2-3361:D3 TK. The set of values is recorded in FIG. 3 and Table 1. The enzyme of the mutant 3-4216:H2 is remarkable by the complete lifting of the inhibition by the GCV substrate and by the increase in the rate of phosphorylation of GCV. The initial rate of phosphorylation of GCV with this mutant is multiplied by a factor of 7, relative to the wild-type enzyme, and a factor of 2.8 relative to the mutant 2-865:H12. Furthermore, the mutant 3-4216:H2 possesses a lower catalytic activity for thymidine phosphorylation than the wild-type enzyme and the other mutants 1537:E4, 2-865:H12 and 2-3361:D3, as indicated by the Kcat/Km values in Table 1.

EXAMPLE 5

CONSTRUCTION OF VECTORS FOR THE EXPRESSION OF TK VARIANTS

This example describes the construction of vectors which can be used for the in vitro or in vivo transfer of the nucleic acid sequences of the invention.

5.1—Construction of Plasmid Vectors

To do this, commercial vectors such as the vectors pZeoSV, pSV2pcDNA3 and the like can be used.

The vector pSV2, described in DNA Cloning, A practical approach Vol. 2, D. M. Glover (Ed) IRL Press, Oxford, Washington D.C., 1985. This vector is a eukaryotic expression vector. The nucleic acids coding for the TK variants were inserted into this vector at the HpaI-EcoRV sites. They are thus placed under the control of the promoter of the SV40 virus enhancer.

The vector pCDNA3 (Invitrogen). This is also a eukaryotic expression vector. The nucleic acid sequences coding for the TK variants of the invention are thus placed in this vector under the As regards the genes coding for wild-type HSVI-TK and control of the CMV early promoter. All the constructions described in Example 1 were introduced into this vector between the HindIII/NotI sites in order to be tested in the different in vivo evaluation systems.

As regards the gene coding for the wild-type HSV1-TK and that of the mutant 2-865:H12, constructs which were prepared with the plasmid pXL2990. This vector originating from pBSK (Stratagen) comprises the CMV promoter/enhancer amplified by PCR from the plasmid PGCN (Tanaka et al., 1990, Cell 60, p. 375). The HSV1-TK gene was amplified by PCR with the aid of the plasmid pBTK1 (see Example 1.1) by creating NcoI and AvrII sites at the ATG and TGA codons respectively. This gene was then cloned downstream of the CMV promoter of pXL2990 and upstream of the SV40 late polyadenylation sequence (amplified by PCR with the aid of the plasmid pGL3basic (Promega)) in order to generate the plasmid pXL3022. In a similar manner, the HSV1-TK gene derived from the mutant 2-865:H12 was amplified by PCR with the aid of the plasmid pXL2843 (see Example 3.4) and then cloned downstream of the CMV promoter of pXL2990 and upstream of the SV40 late polyadenylation sequence in order to generate the plasmid pXL3037, see FIG. 4.

5.2—Construction of Viral Vectors

According to a particular embodiment, the invention lies in the construction and use of viral vectors permitting the in vivo transfer and expression of the nucleic acids as defined above.

As regards adenoviruses more especially, different serotypes, the structure and properties of which vary somewhat, have been characterized. Among these serotypes, it is preferable to use, in the context of the present invention, human adenoviruses type 2 or 5 (Ad 2 or Ad 5) or adenoviruses of animal origin (see Application WO 94/26914). Among adenoviruses of animal origin which can be used in the context of the present invention, adenoviruses of canine, bovine, murine (e.g.: Mav1, Beard et al., Virology 75 (1990) 81), ovine, porcine, avian or alternatively simian (e.g.: SAV) may be mentioned. Preferably, the adenovirus of animal origin is a canine adenovirus, and more preferably a CAV-2 adenovirus [strain Manhattan or A26/61 (ATCC VR-800), for example]. It is preferable to use adenoviruses of human or canine or mixed origin in the context of the invention.

Preferably, the defective adenoviruses of the invention comprise the ITRs, a sequence permitting encapsidation and a nucleic acid according to the invention. Still more preferably, in the genome of the adenoviruses of the invention, the E1 region at least is non-functional. The viral gene in question may be rendered non-functional by any technique known to a person skilled in the art, and in particular by total elimination, substitution, partial deletion or addition of one or more bases in the gene or genes in question. Such modifications may be obtained in vitro (on the isolated DNA) or in situ, for example by means of genetic engineering techniques, or alternatively by treatment by means of mutagenic agents. Other regions may also be modified, and in particular the E3 (WO 95/02697), E2 (WO 94/28938), E4 (WO 94/28152, WO 94/12649, WO 95/02697) and L5 (WO 95/02697) regions. According to a preferred embodiment, the adenovirus according to the invention comprises a deletion in the E1 and E4 regions. According to another preferred embodiment, it comprises a deletion in the E1 region, into which are inserted the E4 region and the nucleic acid sequence of the invention (see FR 94/13355). In the viruses of the invention, the deletion in the E1 region preferably extends from nucleotides 455 to 3329 on the Ad5 adenovirus sequence.

The defective recombinant adenoviruses according to the invention may be prepared by any technique known to a person skilled in the art (Levrero et al., Gene 101 (1991) 195, EP 185,573; Graham, EMBO J. 3 (1984) 2917). In particular, they may be prepared by homologous recombination between an adenovirus and a plasmid carrying, inter alia, the claimed nucleic acid sequence. Homologous recombination takes place after cotransfection of the said adenovirus and said plasmid into a suitable cell line. The cell line used should preferably (i) be transformable by the said elements, and (ii) contain the sequences capable of complementing the portion of the genome of the defective adenovirus, preferably in integrated form in order to avoid risks of recombination. As an example of a line, there may be mentioned the human embryonic kidney line 293 (Graham et al., J. Gen. Virol. 36 (1977) 59) which contains, in particular, integrated in its genome, the left-hand portion of the genome of an Ad5 adenovirus (12%), or lines capable of complementing the E1 and E4 functions as are described, in particular, in Applications Nos. WO 94/26914 and WO 95/02697.

Thereafter, the adenoviruses which have multiplied are recovered and purified according to standard techniques of molecular biology, as illustrated in the examples.

More especially, the adenoviral constructs according to the invention are obtained in accordance with the following protocol:

They were constructed according to the technology described in patent WO96/25506 to which reference will be made for the detailed description of the plasmids mentioned below. For that, the shuttle plasmid pACK3 was used; it originates from ColE1 and contains i) the gene which confers resistance to kanamycin, ii) the *B. subtilis* sacB gene, iii) the ITR-Psi sequences (position 1-386 of the Ad5 adenovirus) separated from the sequences containing the gene coding for the PIX protein (position 3447–4415 of the Ad4 adenovirus) by the EcoRV and SalI restriction sites. The eukaryotic expression cassettes of the plasmids pXL3022 and pXL3037 were cloned between the EcoRV and SalI sites of the shuttle plasmid pACK3 in order to form the plasmids pXL3050 and 3051 respectively, see FIG. 4. By double homologous recombination with the aid of the adenoviral plasmid pXL2822 (described by J. Crouzet et al., 1997, Proc. Natl. Acad. Sci. 94, in press), the adenoviral plasmids pXL3075 and 3076 were generated, respectively. These plasmids were digested with PacI and transfected into the human cell line 293 in order to produce the viruses ADV3075 and ADV3076. These viruses are deleted in the E1 and E3 regions and which contain respectively the cassettes for expression of the HSV1-TK genes for the wild-type enzyme and for the mutant 2-865:H12.

Adeno-associated viruses (AAV) are, for their part, relatively small-sized DNA viruses which integrate stably and in a site-specific manner in the genome of the cells they infect. They are capable of infecting a broad range of cells without inducing an effect on cell growth, morphology or differentiation. Moreover, they do not appear to be implicated in pathologies in man. The AAV genome has been cloned, sequenced and characterized. It comprises approximately 4,700 bases, and contains at each end an inverted repeat region (ITR) of approximately 145 bases, serving as origin of replication for the virus. The remainder of the genome is divided into 2 essential regions carrying the encapsidation functions: the left-hand portion of the genome, which contains the rep gene involved in the viral replication and expression of the viral genes; and the right-hand portion of the genome, which contains the cap gene coding for the capsid proteins of the virus.

The use of vectors derived from AAV for the transfer of genes in vitro and in vivo has been described in the literature (see, in particular, WO 91/18088; WO 93/09239; U.S. Pat. No. 4,797,368, U.S. Pat. No. 5,139,941, EP 488,528). These applications describe different constructions derived from AAV, in which the rep and/or cap genes are deleted and replaced by a gene of interest, and their use for transferring the said gene of interest in vitro (to cells in culture) or in vivo (directly into a body). The defective recombinant AAVs according to the invention may be prepared by cotransfection, into a cell line infected with a human helper virus (for example an adenovirus), of a plasmid containing a nucleic acid sequence of the invention, of interest, flanked by two inverted repeat regions (ITR) of AAV, and a plasmid carrying the encapsidation genes (rep and cap genes) of AAV. A cell line which can be used is, for example, the line 293. The recombinant AAVs produced are then purified by standard techniques.

Regarding herpesviruses and retroviruses, the construction of recombinant vectors has been amply described in the literature: see, in particular, Breakfield et al., New Biologist 3 (1991) 203; EP 453242, EP 178220, Bernstein et al., Genet. Eng. 7 (1985) 235; McCormick, BioTechnology 3 (1985) 689, and the like. In particular, retroviruses are integrative viruses which selectively infect dividing cells. They hence constitute vectors of interest for cancer applications. The retrovirus genome essentially comprises two LTRs, an encapsidation sequence and three coding regions (gag, pol and env). In the recombinant vectors derived from retroviruses, the gag, pol and env genes are generally deleted wholly or partially, and replaced by a heterologous nucleic acid sequence of interest. These vectors may be produced from different types of retrovirus such as, in particular, MoMuLV (Moloney murine leukaemia virus; also designated MoMLV), MSV (Moloney murine sarcoma virus), HaSV (Harvey sarcoma virus), SNV (spleen necrosis virus), RSV (Rous sarcoma virus) or alternatively Friend virus.

To construct recombinant retroviruses according to the invention containing a nucleic acid sequence according to the invention, a plasmid containing, in particular, the LTRs, the encapsidation sequence and the said nucleic acid sequence is constructed, and then used to transfect a so-called encapsidation cell line capable of providing in trans the retroviral functions which are deficient in the plasmid. Generally, the encapsidation lines are hence capable of expressing the gag, pol and env genes. Such encapsidation lines have been described in the prior art, and in particular the line PA317 (U.S. Pat. No. 4,861,719), the line PsiCRIP (WO 90/02806) and the line GP+envAm–12 (WO 89/07150). Moreover, the recombinant retroviruses can contain modifications in the LTRs to eliminate transcriptional activity, as well as extended encapsidation sequences containing a portion of the gag gene (Bender et al., J. Virol. 61 (1987) 1639). The recombinant retroviruses produced are then purified by standard techniques.

To implement the present invention, it is most especially advantageous to use a defective recombinant adenovirus or retrovirus. These vectors possess, in effect, especially advantageous properties for the transfer of suicide genes into tumour cells.

5.3—Chemical Vectors

Among the synthetic vectors developed, it is preferable to use, in the context of the invention, cationic polymers of the polylysine, (LKLK)n, (LKKL)n, polyethylenimine and DEAE-dextran type, or alternatively lipofectants or cationic lipids. They possess the property of condensing DNA and of promoting its combination with the cell membrane. Among the latter compounds, there may be mentioned lipopolyamines (lipofectamine, transfectam, and the like), various cationic or neutral lipids (DOTMA, DOGS, DOPE, and the like) and also peptides of nuclear origin. In addition, the concept of receptor-mediated, targeted transfection has been developed, which turns to good account the principle of condensing DNA by means of the cationic polymer while directing the binding of the complex to the membrane as a result of a chemical coupling between the cationic polymer and the ligand for a membrane receptor present at the surface of the cell type which it is desired to graft. Targeting of the transferrin or insulin receptor or of the asialoglycoprotein receptor of hepatocytes has thus been described. The preparation of the composition according to the invention using such a chemical vector is carried out according to any technique known to a person skilled in the art, generally by simply bringing the different components into contact.

What is claimed is:

1. A nucleic acid coding for a herpes simplex virus type 1 thymidine kinase variant, wherein the variant has a mutation in the region corresponding to the ATP-binding site, and an additional one or more mutations in the N-terminal or C-terminal regions, the mutations selected from the following group or from a mutation resulting in a degenerate coding variant of any in the following group:

adenine substituting for the guanine at position 180 (G180A);

adenine substituting for the guanine at position 16 (G16A);

adenine substituting for the guanine at position 28 (G28A);

adenine substituting for the guanine at position 30 (G30A);

adenine substituting for the guanine at positions 28 and 30 (G28A and G30A);

thymine substituting for the cytosine at position 591 (C591T);

thymine substituting for the cytosine at position 892 (C892T);

thymine substituting for the cytosine at positions 591 and 892 (C591T and C892T);

adenine substituting for the guanine at position 1010 (G1010A);

adenine substituting for the guanine at position 1011 (G1011A);

adenine substituting for the guanine at positions 1010 and 1011 (G1010A and G1011A);

and adenine substituting for the guanine at positions 1010 and 1011 and a thymine substituting for the cytosine at positions 591 and 892 (G1010A; G1011A; C591T; and C892T).

2. The nucleic acid of claim 1, having a mutation at position 180.

3. The nucleic acid of claim 1, having a N-terminal mutation at position 16.

4. The nucleic acid of claim 1, having a N-terminal mutation at position 28.

5. The nucleic acid of claim 1, having a N-terminal mutation at position 30.

6. The nucleic acid of claim 1, having N-terminal mutations at positions 28 and 30.

7. The nucleic acid of claim 1, having a C-terminal mutation at position 591.

8. The nucleic acid of claim 1, having a C-terminal mutation at position 892.

9. The nucleic acid of claim 1, having C-terminal mutations at positions 591 and 892.

10. The nucleic acid of claim 1, having a C-terminal mutation at position 1010.

11. The nucleic acid of claim 1, having a C-terminal mutation at position 1011.

12. The nucleic acid of claim 1, having C-terminal mutations at positions 1010 and 1011.

13. The nucleic acid of claim 1, having C-terminal mutations at positions 591, 892, 1010, and 1011.

14. The nucleic acid of claim 1, having the sequence selected from the group consisting of SEQ ID No: 3, SEQ ID No: 7, SEQ ID No: 9, and SEQ ID No: 11.

15. A thymidine kinase variant comprising an ATP-binding site motif of SEQ ID No: 1 or SEQ ID No: 2, having a substitution mutation in SEQ ID No: 1 or SEQ ID No: 2, and having an additional one or more substitution mutations in the C-terminal or N-terminal regions, the mutations selected from the following sites corresponding to herpes simplex virus type 1 thymidine kinase:

methionine at position 60; alanine at position 10; glycine at position 6; arginine at position 337; methionine at position 60 and alanine at position 10; methionine at position 60 and alanine at position 10 and arginine at position 337; methionine at position 60 and glycine at position 6.

16. The thymidine kinase variant of claim 15, comprising a substitution of the methionine at position 60 with an isoleucine.

17. The thymidine kinase variant of claim 15, which is mutant 1537:E4.

18. The thymidine kinase variant of claim 15, comprising a substitution of the methionine at position 60 with an isoleucine and a substitution of the alanine at position 10 with a threonine.

19. The thymidine kinase variant of claim 15, comprising a substitution of the methionine at position 60 with an isoleucine and a substitution of the glycine at position 6 with a serine.

20. The thymidine kinase variant of claim 15, which is mutant 2-865:H12.

21. The thymidine kinase variant of claim 15, which is mutant 2-3361:D3.

22. The thymidine kinase variant of claim 15, which is mutant 3-4216:H12.

23. The thymidine kinase variant of claim 15, wherein a C-terminal mutation comprises a mutation between amino acids 320 to 350.

24. The thymidine kinase variant of claim 23, wherein a C-terminal mutation comprises a mutation between amino acids 325 to 345.

25. The thymidine kinase variant of claim 24, wherein a C-terminal mutation comprises a mutation between amino acids 330 to 343.

26. The thymidine kinase variant of claim 25, wherein a C-terminal mutation comprises a mutation between amino acids 335 to 340.

27. The thymidine kinase variant of claim 15, comprising a substitution of the methionine at position 60 with an isoleucine, a substitution of the alanine at position 10 with a threonine, and a substitution of the arginine at position 337 with a glutamine.

28. An expression vector comprising the nucleic acid of claim 1.

29. The expression vector of claim 28, which is a recombinant adenovirus vector.

30. The expression vector of claim 29, wherein the vector is replication defective.

31. A composition comprising the vector of claim 28.

32. The composition of claim 31, wherein the vector is an adenovirus vector.

33. The composition of claim 32, wherein the vector is replication defective.

34. The composition of claim 31, wherein the vector is a viral vector.

35. A composition for administration to a human comprising the thymidine kinase variant of claim 15.

36. A method of using a composition of claim 36, comprising administering the composition in an amount effective to transform a prodrug into a toxic agent to eliminate a dividing cell.

37. A method for treating hyperproliferative disorders comprising the method of claim 35, wherein the composition is administered to a subject suffering from a hyperproliferative disorder.

* * * * *

UNITED STATES PATENT AND TRADEMARK OFFICE
CERTIFICATE OF CORRECTION

PATENT NO.    : 6,207,150 B1
DATED         : March 27, 2001
INVENTOR(S)   : Joël Crouzet et al.

It is certified that error appears in the above-identified patent and that said Letters Patent is hereby corrected as shown below:

<u>Title page,</u>
Item [86], change "PCT/ER97/00193" to -- PCT/FR97/00193 --.

<u>Column 44,</u>
Line 29, delete "claim 36" and insert -- claim 35 --.

Signed and Sealed this

Sixth Day of November, 2001

Attest:

NICHOLAS P. GODICI
*Attesting Officer*   *Acting Director of the United States Patent and Trademark Office*

SEQUENCE LISTING

```
<160> NUMBER OF SEQ ID NOS: 12

<210> SEQ ID NO 1
<211> LENGTH: 8
<212> TYPE: PRT
<213> ORGANISM: herpes simplex virus 7
<220> FEATURE:
<221> NAME/KEY: PEPTIDE
<222> LOCATION: (2)..(5)
<223> OTHER INFORMATION: Xaa at positions 2-5 can be any amino acid.
<220> FEATURE:
<221> NAME/KEY: PEPTIDE
<222> LOCATION: (8)
<223> OTHER INFORMATION: Xaa at position 8 can be threonine or Serine.

<400> SEQUENCE: 1

Gly Xaa Xaa Xaa Xaa Gly Lys Xaa
 1               5

<210> SEQ ID NO 2
<211> LENGTH: 8
<212> TYPE: PRT
<213> ORGANISM: herpes simplex virus 7

<400> SEQUENCE: 2

Gly Pro His Gly Met Gly Lys Thr
 1               5

<210> SEQ ID NO 3
<211> LENGTH: 1131
<212> TYPE: DNA
<213> ORGANISM: herpes simplex virus 7
<220> FEATURE:
<221> NAME/KEY: CDS
<222> LOCATION: (1)..(1131)

<400> SEQUENCE: 3 atg gct tcg tac ccc ggc cat caa cac gcg tct gcg ttc gac cag gct        48
Met Ala Ser Tyr Pro Gly His Gln His Ala Ser Ala Phe Asp Gln Ala
 1               5                  10                  15 gcg cgt tct cgc ggc cat agc aac cga cgt acg gcg ttg cgc cct cgc        96
Ala Arg Ser Arg Gly His Ser Asn Arg Thr Ala Leu Arg Pro Arg
             20                  25                  30 cgg cag caa gaa gcc acg gaa gtc cgc ccg gag cag aaa atg ccc acg       144
Arg Gln Gln Glu Ala Thr Glu Val Arg Pro Glu Gln Lys Met Pro Thr
         35                  40                  45
```

```
cta ctg cgg gtt tat ata gac ggt ccc cac ggg ata ggg aaa acc acc    192
Leu Leu Arg Val Tyr Ile Asp Gly Pro His Gly Ile Gly Lys Thr Thr
     50                  55                  60 acc acg caa ctg ctg gtg gcc ctg ggt tcg cgc gac gat atc gtc tac    240
Thr Thr Gln Leu Leu Val Ala Leu Gly Ser Arg Asp Asp Ile Val Tyr
 65                  70                  75                  80 gta ccc gag ccg atg act tac tgg cgg gtg ctg ggg gct tcc gag aca    288
Val Pro Glu Pro Met Thr Tyr Trp Arg Val Leu Gly Ala Ser Glu Thr
                 85                  90                  95 atc gcg aac atc tac acc aca caa cac cgc ctc gac cag ggt gag ata    336
Ile Ala Asn Ile Tyr Thr Thr Gln His Arg Leu Asp Gln Gly Glu Ile
            100                 105                 110 tcg gcc ggg gac gcg gcg gtg gta atg aca agc gcc cag ata aca atg    384
Ser Ala Gly Asp Ala Ala Val Val Met Thr Ser Ala Gln Ile Thr Met
        115                 120                 125 ggc atg cct tat gcc gtg acc gac gcc gtt ctg gct cct cat atc ggg    432
Gly Met Pro Tyr Ala Val Thr Asp Ala Val Leu Ala Pro His Ile Gly
    130                 135                 140 ggg gag gct ggg agc tca cat gcc ccg ccc ccg gcc ctc acc ctc atc    480
Gly Glu Ala Gly Ser Ser His Ala Pro Pro Pro Ala Leu Thr Leu Ile
145                 150                 155                 160 ttc gac cgc cat ccc atc gcc gcc ctc ctg tgc tac ccg gcc gcg cgg    528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc    576
Tyr Leu Met Gly Ser Met Thr Pro Gln Ala Val Leu Ala Phe Val Ala
            180                 185                 190 ctc atc ccg ccg acc ttg ccc ggc acc aac atc gtg ctt ggg gcc ctt    624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc    672
Pro Glu Asp Arg His Ile Asp Arg Leu Ala Lys Arg Gln Arg Pro Gly
    210                 215                 220 gag cgg ctg gac ctg gct atg ctg gct gcg att cgc cgc gtt tac ggg    720
Glu Arg Leu Asp Leu Ala Met Leu Ala Ala Ile Arg Arg Val Tyr Gly
225                 230                 235                 240 cta ctt gcc aat acg gtg cgg tat ctg cag tgc ggc ggg tcg tgg cgg    768
Leu Leu Ala Asn Thr Val Arg Tyr Leu Gln Cys Gly Gly Ser Trp Arg
                245                 250                 255 gag gac tgg gga cag ctt tcg ggg acg gcc gtg ccc ccc cag ggt gcc    816
Glu Asp Trp Gly Gln Leu Ser Gly Thr Ala Val Pro Pro Gln Gly Ala
            260                 265                 270 gag ccc cag agc aac gcg ggc cca cga ccc cat atc ggg gac acg tta    864
Glu Pro Gln Ser Asn Ala Gly Pro Arg Pro His Ile Gly Asp Thr Leu
        275                 280                 285 ttt acc ctg ttt cgg gcc ccc gag ttg ctg gcc ccc aac ggc gac ctg    912
Phe Thr Leu Phe Arg Ala Pro Glu Leu Leu Ala Pro Asn Gly Asp Leu
    290                 295                 300 tat aac gtg ttt gcc tgg gcc ttg gac gtc ttg gcc aaa cgc ctc cgt    960
Tyr Asn Val Phe Ala Trp Ala Leu Asp Val Leu Ala Lys Arg Leu Arg
305                 310                 315                 320 tcc atg cac gtc ttt atc ctg gat tac gac caa tcg ccc gcc ggc tgc   1008
Ser Met His Val Phe Ile Leu Asp Tyr Asp Gln Ser Pro Ala Gly Cys
                325                 330                 335 cgg gac gcc ctg ctg caa ctt acc tcc ggg atg gtc cag acc cac gtc   1056
Arg Asp Ala Leu Leu Gln Leu Thr Ser Gly Met Val Gln Thr His Val
            340                 345                 350 acc acc ccc ggc tcc ata ccg acg ata tgc gac ctg gcg cgc acg ttt   1104
Thr Thr Pro Gly Ser Ile Pro Thr Ile Cys Asp Leu Ala Arg Thr Phe
        355                 360                 365
```

```
gcc cgg gag atg ggg gag gct aac tga                                    1131
Ala Arg Glu Met Gly Glu Ala Asn
    370                 375
```

<210> SEQ ID NO 4
<211> LENGTH: 376
<212> TYPE: PRT
<213> ORGANISM: herpes simplex virus 7

<400> SEQUENCE: 4

```
Met Ala Ser Tyr Pro Gly His Gln His Ala Ser Ala Phe Asp Gln Ala
  1               5                  10                  15

Ala Arg Ser Arg Gly His Ser Asn Arg Arg Thr Ala Leu Arg Pro Arg
             20                  25                  30

Arg Gln Gln Glu Ala Thr Glu Val Arg Pro Glu Gln Lys Met Pro Thr
         35                  40                  45

Leu Leu Arg Val Tyr Ile Asp Gly Pro His Gly Ile Gly Lys Thr Thr
     50                  55                  60

Thr Thr Gln Leu Leu Val Ala Leu Gly Ser Arg Asp Asp Ile Val Tyr
 65                  70                  75                  80

Val Pro Glu Pro Met Thr Tyr Trp Arg Val Leu Gly Ala Ser Glu Thr
                 85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350
```

```
Thr Thr Pro Gly Ser Ile Pro Thr Ile Cys Asp Leu Ala Arg Thr Phe
        355                 360                 365
Ala Arg Glu Met Gly Glu Ala Asn
    370                 375

<210> SEQ ID NO 5
<211> LENGTH: 30
<212> TYPE: DNA
<213> ORGANISM: herpes simplex virus 7

<400> SEQUENCE: 5
ttatgaattc atatggcttc gtaccccggc                                       30

<210> SEQ ID NO 6
<211> LENGTH: 27
<212> TYPE: DNA
<213> ORGANISM: herpes simplex virus 7

<400> SEQUENCE: 6
ttatttctag aggtcgaaga tgagggt                                          27

<210> SEQ ID NO 7
<211> LENGTH: 1131
<212> TYPE: DNA
<213> ORGANISM: herpes simplex virus 7
<220> FEATURE:
<221> NAME/KEY: CDS
<222> LOCATION: (1)..(1131)

<400> SEQUENCE: 7 atg gct tcg tac ccc agc cat caa cac gcg tct gcg ttc gac cag gct        48
Met Ala Ser Tyr Pro Ser His Gln His Ala Ser Ala Phe Asp Gln Ala
  1               5                  10                  15 gcg cgt tct cgc ggc cat agc aac cga cgt acg gcg ttg cgc cct cgc        96
Ala Arg Ser Arg Gly His Ser Asn Arg Arg Thr Ala Leu Arg Pro Arg
             20                  25                  30 cgg cag caa gaa gcc acg gaa gtc cgc ccg gag cag aaa atg ccc acg       144
Arg Gln Gln Glu Ala Thr Glu Val Arg Pro Glu Gln Lys Met Pro Thr
         35                  40                  45 cta ctg cgg gtt tat ata gac ggt ccc cac ggg ata ggg aaa acc acc       192
Leu Leu Arg Val Tyr Ile Asp Gly Pro His Gly Ile Gly Lys Thr Thr
     50                  55                  60 acc acg caa ctg ctg gtg gcc ctg ggt tcg cgc gac gat atc gtc tac       240
Thr Thr Gln Leu Leu Val Ala Leu Gly Ser Arg Asp Asp Ile Val Tyr
 65                  70                  75                  80 gta ccc gag ccg atg act tac tgg cgg gtg ctg ggg gct tcc gag aca       288
Val Pro Glu Pro Met Thr Tyr Trp Arg Val Leu Gly Ala Ser Glu Thr
                 85                  90                  95 atc gcg aac atc tac acc aca caa cac cgc ctc gac cag ggt gag ata       336
Ile Ala Asn Ile Tyr Thr Thr Gln His Arg Leu Asp Gln Gly Glu Ile
            100                 105                 110 tcg gcc ggg gac gcg gcg gtg gta atg aca agc gcc cag ata aca atg       384
Ser Ala Gly Asp Ala Ala Val Val Met Thr Ser Ala Gln Ile Thr Met
        115                 120                 125 ggc atg cct tat gcc gtg acc gac gcc gtt ctg gct cct cat atc ggg       432
Gly Met Pro Tyr Ala Val Thr Asp Ala Val Leu Ala Pro His Ile Gly
    130                 135                 140 ggg gag gct ggg agc tca cat gcc ccg ccc ccg gcc ctc acc ctc atc       480
Gly Glu Ala Gly Ser Ser His Ala Pro Pro Pro Ala Leu Thr Leu Ile
145                 150                 155                 160
```

```
ttc gac cgc cat ccc atc gcc gcc ctc ctg tgc tac ccg gcc gcg cgg      528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc      576
Tyr Leu Met Gly Ser Met Thr Pro Gln Ala Val Leu Ala Phe Val Ala
            180                 185                 190 ctc atc ccg ccg acc ttg ccc ggc acc aac atc gtg ctt ggg gcc ctt      624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc      672
Pro Glu Asp Arg His Ile Asp Arg Leu Ala Lys Arg Gln Arg Pro Gly
    210                 215                 220 gag cgg ctg gac ctg gct atg ctg gct gcg att cgc cgc gtt tac ggg      720
Glu Arg Leu Asp Leu Ala Met Leu Ala Ala Ile Arg Arg Val Tyr Gly
225                 230                 235                 240 cta ctt gcc aat acg gtg cgg tat ctg cag tgc ggc ggg tcg tgg cgg      768
Leu Leu Ala Asn Thr Val Arg Tyr Leu Gln Cys Gly Gly Ser Trp Arg
                245                 250                 255 gag gac tgg gga cag ctt tcg ggg acg gcc gtg ccg ccc cag ggt gcc      816
Glu Asp Trp Gly Gln Leu Ser Gly Thr Ala Val Pro Pro Gln Gly Ala
            260                 265                 270 gag ccc cag agc aac gcg ggc cca cga ccc cat atc ggg gac acg tta      864
Glu Pro Gln Ser Asn Ala Gly Pro Arg Pro His Ile Gly Asp Thr Leu
        275                 280                 285 ttt acc ctg ttt cgg gcc ccc gag ttg ctg gcc ccc aac ggc gac ctg      912
Phe Thr Leu Phe Arg Ala Pro Glu Leu Leu Ala Pro Asn Gly Asp Leu
    290                 295                 300 tat aac gtg ttt gcc tgg gcc ttg gac gtc ttg gcc aaa cgc ctc cgt      960
Tyr Asn Val Phe Ala Trp Ala Leu Asp Val Leu Ala Lys Arg Leu Arg
305                 310                 315                 320 tcc atg cac gtc ttt atc ctg gat tac gac caa tcg ccc gcc ggc tgc     1008
Ser Met His Val Phe Ile Leu Asp Tyr Asp Gln Ser Pro Ala Gly Cys
                325                 330                 335 cgg gac gcc ctg ctg caa ctt acc tcc ggg atg gtc cag acc cac gtc     1056
Arg Asp Ala Leu Leu Gln Leu Thr Ser Gly Met Val Gln Thr His Val
            340                 345                 350 acc acc ccc ggc tcc ata ccg acg ata tgc gac ctg gcg cgc acg ttt     1104
Thr Thr Pro Gly Ser Ile Pro Thr Ile Cys Asp Leu Ala Arg Thr Phe
        355                 360                 365 gcc cgg gag atg ggg gag gct aac tga                                 1131
Ala Arg Glu Met Gly Glu Ala Asn
    370                 375

<210> SEQ ID NO 8
<211> LENGTH: 376
<212> TYPE: PRT
<213> ORGANISM: herpes simplex virus 7

<400> SEQUENCE: 8

Met Ala Ser Tyr Pro Ser His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Ile Gly Lys Thr Thr
    50                  55                  60

Thr Thr Gln Leu Leu Val Ala Leu Gly Ser Arg Asp Asp Ile Val Tyr
65                  70                  75                  80
```

```
Val Pro Glu Pro Met Thr Tyr Trp Arg Val Leu Gly Ala Ser Glu Thr
             85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 9
<211> LENGTH: 1131
<212> TYPE: DNA
<213> ORGANISM: herpes simplex virus 7
<220> FEATURE:
<221> NAME/KEY: CDS
<222> LOCATION: (1)..(1131)

<400> SEQUENCE: 9 atg gct tcg tac ccc ggc cat caa cac aca tct gcg ttc gac cag gct      48
Met Ala Ser Tyr Pro Gly His Gln His Thr Ser Ala Phe Asp Gln Ala
  1               5                  10                  15 gcg cgt tct cgc ggc cat agc aac cga cgt acg gcg ttg cgc cct cgc      96
Ala Arg Ser Arg Gly His Ser Asn Arg Arg Thr Ala Leu Arg Pro Arg
             20                  25                  30 cgg cag caa gaa gcc acg gaa gtc cgc ccg gag cag aaa atg ccc acg     144
Arg Gln Gln Glu Ala Thr Glu Val Arg Pro Glu Gln Lys Met Pro Thr
         35                  40                  45
```

-continued

```
cta ctg cgg gtt tat ata gac ggt ccc cac ggg ata ggg aaa acc acc    192
Leu Leu Arg Val Tyr Ile Asp Gly Pro His Gly Ile Gly Lys Thr Thr
     50                  55                  60 acc acg caa ctg ctg gtg gcc ctg ggt tcg cgc gac gat atc gtc tac    240
Thr Thr Gln Leu Leu Val Ala Leu Gly Ser Arg Asp Asp Ile Val Tyr
 65                  70                  75                  80 gta ccc gag ccg atg act tac tgg cgg gtg ctg ggg gct tcc gag aca    288
Val Pro Glu Pro Met Thr Tyr Trp Arg Val Leu Gly Ala Ser Glu Thr
                 85                  90                  95 atc gcg aac atc tac acc aca caa cac cgc ctc gac cag ggt gag ata    336
Ile Ala Asn Ile Tyr Thr Thr Gln His Arg Leu Asp Gln Gly Glu Ile
            100                 105                 110 tcg gcc ggg gac gcg gcg gtg gta atg aca agc gcc cag ata aca atg    384
Ser Ala Gly Asp Ala Ala Val Val Met Thr Ser Ala Gln Ile Thr Met
        115                 120                 125 ggc atg cct tat gcc gtg acc gac gcc gtt ctg gct cct cat atc ggg    432
Gly Met Pro Tyr Ala Val Thr Asp Ala Val Leu Ala Pro His Ile Gly
    130                 135                 140 ggg gag gct ggg agc tca cat gcc ccg ccc ccg gcc ctc acc ctc atc    480
Gly Glu Ala Gly Ser Ser His Ala Pro Pro Pro Ala Leu Thr Leu Ile
145                 150                 155                 160 ttc gac cgc cat ccc atc gcc gcc ctc ctg tgc tac ccg gcc gcg cgg    528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc    576
Tyr Leu Met Gly Ser Met Thr Pro Gln Ala Val Leu Ala Phe Val Ala
            180                 185                 190 ctc atc ccg ccg acc ttg ccc ggc acc aac atc gtg ctt ggg gcc ctt    624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc    672
Pro Glu Asp Arg His Ile Asp Arg Leu Ala Lys Arg Gln Arg Pro Gly
    210                 215                 220 gag cgg ctg gac ctg gct atg ctg gct gcg att cgc cgc gtt tac ggg    720
Glu Arg Leu Asp Leu Ala Met Leu Ala Ala Ile Arg Arg Val Tyr Gly
225                 230                 235                 240 cta ctt gcc aat acg gtg cgg tat ctg cag tgc ggc ggg tcg tgg cgg    768
Leu Leu Ala Asn Thr Val Arg Tyr Leu Gln Cys Gly Gly Ser Trp Arg
                245                 250                 255 gag gac tgg gga cag ctt tcg ggg acg gcc gtg ccg ccc cag ggt gcc    816
Glu Asp Trp Gly Gln Leu Ser Gly Thr Ala Val Pro Pro Gln Gly Ala
            260                 265                 270 gag ccc cag agc aac gcg ggc cca cga ccc cat atc ggg gac acg tta    864
Glu Pro Gln Ser Asn Ala Gly Pro Arg Pro His Ile Gly Asp Thr Leu
        275                 280                 285 ttt acc ctg ttt cgg gcc ccc gag ttg ctg gcc ccc aac ggc gac ctg    912
Phe Thr Leu Phe Arg Ala Pro Glu Leu Leu Ala Pro Asn Gly Asp Leu
    290                 295                 300 tat aac gtg ttt gcc tgg gcc ttg gac gtc ttg gcc aaa cgc ctc cgt    960
Tyr Asn Val Phe Ala Trp Ala Leu Asp Val Leu Ala Lys Arg Leu Arg
305                 310                 315                 320 tcc atg cac gtc ttt atc ctg gat tac gac caa tcg ccc gcc ggc tgc   1008
Ser Met His Val Phe Ile Leu Asp Tyr Asp Gln Ser Pro Ala Gly Cys
                325                 330                 335 cgg gac gcc ctg ctg caa ctt acc tcc ggg atg gtc cag acc cac gtc   1056
Arg Asp Ala Leu Leu Gln Leu Thr Ser Gly Met Val Gln Thr His Val
            340                 345                 350
```

```
acc acc ccc ggc tcc ata ccg acg ata tgc gac ctg gcg cgc acg ttt    1104
Thr Thr Pro Gly Ser Ile Pro Thr Ile Cys Asp Leu Ala Arg Thr Phe
        355                 360                 365 gcc cgg gag atg ggg gag gct aac tga                                1131
Ala Arg Glu Met Gly Glu Ala Asn
370                 375
```

<210> SEQ ID NO 10
<211> LENGTH: 376
<212> TYPE: PRT
<213> ORGANISM: herpes simplex virus 7

<400> SEQUENCE: 10

```
Met Ala Ser Tyr Pro Gly His Gln His Thr Ser Ala Phe Asp Gln Ala
  1               5                  10                  15

Ala Arg Ser Arg Gly His Ser Asn Arg Arg Thr Ala Leu Arg Pro Arg
                 20                  25                  30

Arg Gln Gln Glu Ala Thr Glu Val Arg Pro Glu Gln Lys Met Pro Thr
             35                  40                  45

Leu Leu Arg Val Tyr Ile Asp Gly Pro His Gly Ile Gly Lys Thr Thr
         50                  55                  60

Thr Thr Gln Leu Leu Val Ala Leu Gly Ser Arg Asp Asp Ile Val Tyr
 65                  70                  75                  80

Val Pro Glu Pro Met Thr Tyr Trp Arg Val Leu Gly Ala Ser Glu Thr
                 85                  90                  95

Ile Ala Asn Ile Tyr Thr Thr Gln His Arg Leu Asp Gln Gly Glu Ile
                100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335
```

```
                                   -continued

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
    370                 375

<210> SEQ ID NO 11
<211> LENGTH: 1131
<212> TYPE: DNA
<213> ORGANISM: herpes simplex virus 7
<220> FEATURE:
<221> NAME/KEY: CDS
<222> LOCATION: (1)..(1131)

<400> SEQUENCE: 11 atg gct tcg tac ccc ggc cat caa cac aca tct gcg ttc gac cag gct        48
Met Ala Ser Tyr Pro Gly His Gln His Thr Ser Ala Phe Asp Gln Ala
 1               5                  10                  15 gcg cgt tct cgc ggc cat agc aac cga cgt acg gcg ttg cgc cct cgc        96
Ala Arg Ser Arg Gly His Ser Asn Arg Arg Thr Ala Leu Arg Pro Arg
             20                  25                  30 cgg cag caa gaa gcc acg gaa gtc cgc ccg gag cag aaa atg ccc acg       144
Arg Gln Gln Glu Ala Thr Glu Val Arg Pro Glu Gln Lys Met Pro Thr
         35                  40                  45 cta ctg cgg gtt tat ata gac ggt ccc cac ggg ata ggg aaa acc acc       192
Leu Leu Arg Val Tyr Ile Asp Gly Pro His Gly Ile Gly Lys Thr Thr
     50                  55                  60 acc acg caa ctg ctg gtg gcc ctg ggt tcg cgc gac gat atc gtc tac       240
Thr Thr Gln Leu Leu Val Ala Leu Gly Ser Arg Asp Asp Ile Val Tyr
 65                  70                  75                  80 gta ccc gag ccg atg act tac tgg cgg gtg ctg ggg gct tcc gag aca       288
Val Pro Glu Pro Met Thr Tyr Trp Arg Val Leu Gly Ala Ser Glu Thr
                 85                  90                  95 atc gcg aac atc tac acc aca caa cac cgc ctc gac cag ggt gag ata       336
Ile Ala Asn Ile Tyr Thr Thr Gln His Arg Leu Asp Gln Gly Glu Ile
            100                 105                 110 tcg gcc ggg gac gcg gcg gtg gta atg aca agc gcc cag ata aca atg       384
Ser Ala Gly Asp Ala Ala Val Val Met Thr Ser Ala Gln Ile Thr Met
        115                 120                 125 ggc atg cct tat gcc gtg acc gac gcc gtt ctg gct cct cat atc ggg       432
Gly Met Pro Tyr Ala Val Thr Asp Ala Val Leu Ala Pro His Ile Gly
    130                 135                 140 ggg gag gct ggg agc tca cat gcc ccg ccc ccg gcc ctc acc ctc atc       480
Gly Glu Ala Gly Ser Ser His Ala Pro Pro Pro Ala Leu Thr Leu Ile
145                 150                 155                 160 ttc gac cgc cat ccc atc gcc gcc ctc ctg tgc tac ccg gcc gcg cgg       528
Phe Asp Arg His Pro Ile Ala Ala Leu Leu Cys Tyr Pro Ala Ala Arg
                165                 170                 175 tac ctt atg ggc agc atg acc ccc cag gcc gtg ctg gcg ttc gtg gcc       576
Tyr Leu Met Gly Ser Met Thr Pro Gln Ala Val Leu Ala Phe Val Ala
            180                 185                 190 ctc atc ccg ccg act ttg ccc ggc acc aac atc gtg ctt ggg gcc ctt       624
Leu Ile Pro Pro Thr Leu Pro Gly Thr Asn Ile Val Leu Gly Ala Leu
        195                 200                 205 ccg gag gac aga cac atc gac cgc ctg gcc aaa cgc cag cgc ccc ggc       672
Pro Glu Asp Arg His Ile Asp Arg Leu Ala Lys Arg Gln Arg Pro Gly
    210                 215                 220 gag cgg ctg gac ctg gct atg ctg gct gcg att cgc cgc gtt tac ggg       720
Glu Arg Leu Asp Leu Ala Met Leu Ala Ala Ile Arg Arg Val Tyr Gly
225                 230                 235                 240
```

```
cta ctt gcc aat acg gtg cgg tat ctg cag tgc ggc ggg tcg tgg cgg      768
Leu Leu Ala Asn Thr Val Arg Tyr Leu Gln Cys Gly Gly Ser Trp Arg
                245                 250                 255 gag gac tgg gga cag ctt tcg ggg acg gcc gtg ccg ccc cag ggt gcc      816
Glu Asp Trp Gly Gln Leu Ser Gly Thr Ala Val Pro Pro Gln Gly Ala
            260                 265                 270 gag ccc cag agc aac gcg ggc cca cga ccc cat atc ggg gac acg tta      864
Glu Pro Gln Ser Asn Ala Gly Pro Arg Pro His Ile Gly Asp Thr Leu
        275                 280                 285 ttt acc ctg ttt cgg gcc ccc gag ttg ttg gcc ccc aac ggc gac ctg      912
Phe Thr Leu Phe Arg Ala Pro Glu Leu Leu Ala Pro Asn Gly Asp Leu
    290                 295                 300 tat aac gtg ttt gcc tgg gcc ttg gac gtc ttg gcc aaa cgc ctc cgt      960
Tyr Asn Val Phe Ala Trp Ala Leu Asp Val Leu Ala Lys Arg Leu Arg
305                 310                 315                 320 tcc atg cac gtc ttt atc ctg gat tac gac caa tcg ccc gcc ggc tgc     1008
Ser Met His Val Phe Ile Leu Asp Tyr Asp Gln Ser Pro Ala Gly Cys
                325                 330                 335 caa gac gcc ctg ctg caa ctt acc tcc ggg atg gtc cag acc cac gtc     1056
Gln Asp Ala Leu Leu Gln Leu Thr Ser Gly Met Val Gln Thr His Val
            340                 345                 350 acc acc ccc ggc tcc ata ccg acg ata tgc gac ctg gcg cgc acg ttt     1104
Thr Thr Pro Gly Ser Ile Pro Thr Ile Cys Asp Leu Ala Arg Thr Phe
        355                 360                 365 gcc cgg gag atg ggg gag gct aac tga                                 1131
Ala Arg Glu Met Gly Glu Ala Asn
    370                 375

<210> SEQ ID NO 12
<211> LENGTH: 376
<212> TYPE: PRT
<213> ORGANISM: herpes simplex virus 7

<400> SEQUENCE: 12

Met Ala Ser Tyr Pro Gly His Gln His Thr Ser Ala Phe Asp Gln Ala
 1               5                  10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Ile Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Ile Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175
```

-continued

```
Tyr Leu Met Gly Ser Met Thr Pro Gln Ala Val Leu Ala Phe Val Ala
            180             185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Gln Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
    370                 375
```